(12) United States Patent
Lamb et al.

(10) Patent No.: US 9,597,667 B2
(45) Date of Patent: Mar. 21, 2017

(54) PALLADIUM, RHENIUM AND ALUMINA CATALYSTS FOR THE SELECTIVE HYDROGENATION OF CARBONYLS, THEIR SYNTHESIS, AND METHODS OF USING THE SAME

(71) Applicant: North Carolina State University, Raleigh, NC (US)

(72) Inventors: H. Henry Lamb, Raleigh, NC (US); Simon T. Thompson, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 15/081,754

(22) Filed: Mar. 25, 2016

(65) Prior Publication Data

US 2016/0279615 A1 Sep. 29, 2016

Related U.S. Application Data

(60) Provisional application No. 62/138,952, filed on Mar. 26, 2015.

(51) Int. Cl.
*B01J 23/656* (2006.01)
*B01J 37/02* (2006.01)
*C07D 307/42* (2006.01)

(52) U.S. Cl.
CPC ......... *B01J 23/6567* (2013.01); *B01J 37/024* (2013.01); *C07D 307/42* (2013.01)

(58) Field of Classification Search
CPC .................................................. B01J 23/6567
USPC ....................................................... 549/502
See application file for complete search history.

(56) References Cited

U.S. PATENT DOCUMENTS

| | | |
|---|---|---|
| 4,550,185 A | 10/1985 | Mabry et al. |
| 4,609,636 A | 9/1986 | Mabry et al. |
| 4,795,733 A | 1/1989 | De Thomas |
| 4,937,384 A | 6/1990 | Dobson |
| 5,061,671 A | 10/1991 | Kitson et al. |
| 5,149,680 A | 9/1992 | Kitson et al. |
| 7,038,094 B2 | 5/2006 | Werpy et al. |
| 7,214,641 B2 | 5/2007 | Schubert et al. |
| 2006/0052239 A1 | 3/2006 | Schubert et al. |
| 2008/0153692 A1 | 6/2008 | Kimmich et al. |
| 2012/0277475 A1 | 11/2012 | Couturier et al. |
| 2013/0331258 A1 | 12/2013 | Hao et al. |

OTHER PUBLICATIONS

Takeda et al., "Selective hydrogenation of higher saturated carboxylic acids to alcohols using a ReOx-Pd/SiO2 catalyst," Catal. Sci. Technol., 2012, 2, 2221-2223.
Zadesenets et al., "Complex Salts [Pd(NH3)4](ReO4)2 and [Pd(NH3)4](MnO4)2: Synthesis, Structure, and Thermal Properties," Russian Journal of Coordination Chemistry, 2006, vol. 32, No. 5, pp. 374-379.
Ziemecki et al., "Surface Mobility of Re2O7 in the System Re7+Pd0/y-Al2O3," Journal of Catalysis 99, 1986, 207-217.
International Search Report and Written Opinion for Application No. PCT/US2016/024364 dated Jun. 20, 2016 (12 pages).

*Primary Examiner* — Taofiq A Solola
(74) *Attorney, Agent, or Firm* — Michael Best & Friedrich LLP

(57) ABSTRACT

Catalysts useful for the selective hydrogenation of carbonyl groups, including for the reduction of aldehydes to alcohols, are described. The catalysts incorporate palladium and rhenium on an alumina support. Methods of making the catalysts, and methods of using the catalysts for the selective hydrogenation of furanyl 2-carbaldehydes to 2-furanmethanols, are also presented.

26 Claims, 24 Drawing Sheets
(4 of 24 Drawing Sheet(s) Filed in Color)

US 9,597,667 B2

PALLADIUM, RHENIUM AND ALUMINA CATALYSTS FOR THE SELECTIVE HYDROGENATION OF CARBONYLS, THEIR SYNTHESIS, AND METHODS OF USING THE SAME

CROSS REFERENCE TO RELATED APPLICATIONS

This application claims the benefit of U.S. Provisional Patent Application Ser. No. 62/138,952, filed on Mar. 26, 2015, which is hereby incorporated by reference in its entirety for all of its teachings.

FIELD OF INVENTION

The disclosure provided herein relates to catalysts, their synthesis, and methods of using the catalysts for the selective hydrogenation of carbonyl groups.

BACKGROUND

Known palladium and rhenium catalysts have been found to be of limited value when used for the hydrogenation of chemical compounds which contain multiple sites of unsaturation because of their lack of selectivity and their propensity for excessive hydrogenation (i.e. over-reduction). Such catalysts are unable to selectively hydrogenate one unsaturated bond in the presence of other sites of unsaturation to produce a desired compound, or instead over-reduce the material. Catalysts that are able to selectively hydrogenate a chemical compound which contains multiple sites of unsaturation, and with high catalytic activity (i.e., high turnover frequency), are needed.

SUMMARY

The present disclosure provides catalysts which may be used for the selective hydrogenation of carbonyl groups such as aldehydes, comprising an alumina support, rhenium adsorbed to the alumina support, and palladium adsorbed to the alumina support, wherein the rhenium is adsorbed to the alumina support before the palladium is adsorbed to the alumina support.

The present disclosure also provides methods of making catalysts for the hydrogenation of an aldehyde, comprising contacting an alumina support with a solution comprising rhenium to provide a first composition comprising an alumina support with rhenium absorbed thereto, and contacting the first composition with a solution comprising palladium to provide a second composition.

The present disclosure also provides methods of hydrogenating a furan-2-carbaldehyde to a 2-furanmethanol, comprising contacting a catalyst comprising rhenium, palladium and an alumina support with the furan-2-carbaldehyde in the presence of hydrogen to provide the 2-furanmethanol, wherein the catalyst was made by sequentially contacting a solution comprising rhenium and a solution comprising palladium with the alumina support; or by forming a salt comprising rhenium and palladium, and contacting a solution comprising the salt with the alumina support.

Other aspects of the disclosure will become apparent by consideration of the detailed description and accompanying drawings.

BRIEF DESCRIPTION OF THE DRAWINGS

The drawings below are supplied in order to facilitate understanding of the Description and Examples provided herein. The patent or application file contains at least one drawing executed in color. Copies of this patent or patent application publication with color drawing(s) will be provided by the Office upon request and payment of the necessary fee.

FIG. 5(a) is spectra from catalysts made with Grace alumina, and FIG. 5(b) is spectra from catalysts made with Strem alumina.

FIG. 6(a) are profiles from catalysts made with Grace alumina, and FIG. 6(b) are profiles from catalysts made with Strem alumina.

FIG. 8(a) are profiles from catalysts made with Grace alumina, and FIG. 8(b) are profiles from catalysts made with Strem alumina.

FIG. 9(a) are profiles from catalysts made with Grace alumina, and FIG. 9(b) are profiles from catalysts made with Strem alumina.

DETAILED DESCRIPTION

Figure 1:
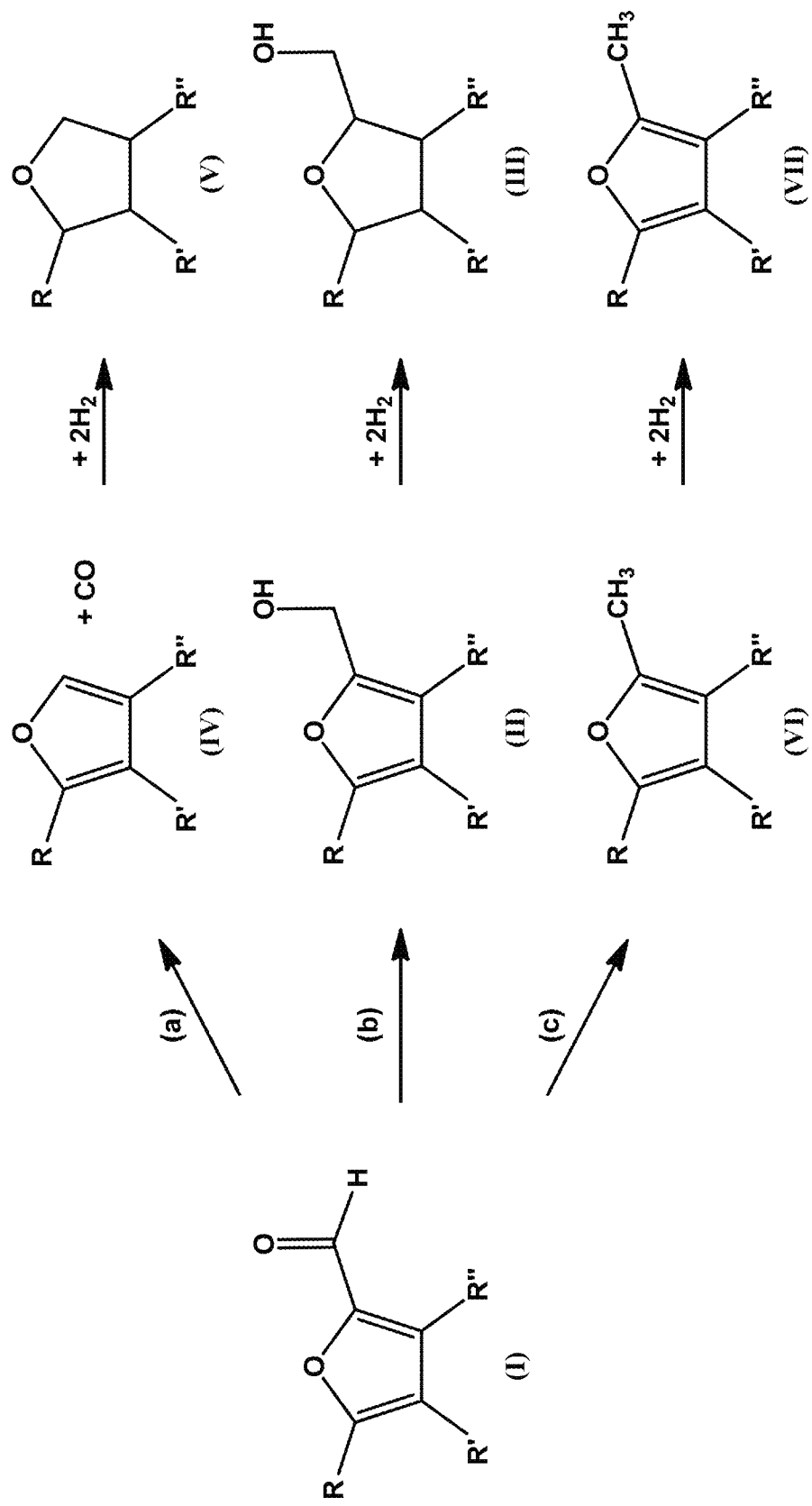
FIG. 1 is a reaction scheme showing potential reaction products from the hydrogenation of an exemplary aldehyde.

Before any embodiments of the invention are explained in detail, it is to be understood that the invention is not limited in its application to the details of construction and the arrangement of components set forth in the following description or illustrated in the drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof, as well as additional items.

It also should be understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

It should be understood that, as used herein, the term "about" is synonymous with the term "approximately." Illustratively, the use of the term "about" indicates that a value includes values slightly outside the cited values. Variation may be due to conditions such as experimental error, manufacturing tolerances, and variations in equilibrium conditions. In some embodiments, the term "about" includes the cited value plus or minus 10%. In all cases, where the term "about" has been used to describe a value, it should be appreciated that this disclosure also supports the exact value.

Reference throughout this specification to "one embodiment," "an embodiment," or similar language means that a particular feature, structure, or characteristic described in connection with the embodiment is included in at least one embodiment of the invention provided herein. Thus, appearances of the phrases "in one embodiment," "in an embodiment," and similar language throughout this specification may, but do not necessarily, all refer to the same embodiment.

Furthermore, the described features, structures, or characteristics of the methods and compositions provided herein may be combined in any suitable manner in one or more embodiments. In the following description, numerous specific details are provided, to provide a thorough understanding of embodiments. One skilled in the relevant art will recognize, however, that the embodiments may be practiced without one or more of the specific details, or with other methods, components, or materials. In other instances, well-known structures, materials, or operations are not shown or described in detail to avoid obscuring aspects of the embodiments.

The inability of conventional catalysts made with palladium and rhenium to perform selective hydrogenations without over-reduction is problematic. The importance of selectivity can be illustrated with the hydrogenation of a cyclic unsaturated aldehyde to a cyclic unsaturated alcohol. FIG. 1 shows potential products formed in the hydrogenation of an optionally substituted furan-2-carbaldehyde (I), which contains a furfural core structure. Hydrogenation of the aldehyde moiety to produce the corresponding alcohol, 2-furanmethanol (II), can occur following route (b). The 2-furanmethanol (II) may be further hydrogenated to the corresponding tetrahydrofuran alcohol product (III). Alternatively or in addition, the furan-2-carbaldehyde (I) may undergo decarbonylation of the aldehyde group following route (a) during a hydrogenation, to produce the furan (IV). The furan (IV) may further undergo reduction of the ring to form the tetrahydrofuran (V). Following route (c), a furan-2-carbaldehyde (I) may undergo hydrodeoxygenation (HDO) of the aldehyde moiety to form a 2-methyl furan (VI), and further hydrogenation to the 2-methyl tetrahydrofuran product (VII). The hydrogenation of the furan ring may also occur prior to hydrogenation of the aldehyde moiety, decarbonylation or hydrodeoxygenation, and numerous ring-opened products are also possible (although not shown in FIG. 1). Depending on the catalyst used for the hydrogenation, different selectivity and efficiency may be achieved for a particular reactant and product. High selectivity for the desired product, whichever product it may be, is important in the hydrogenation of such compounds.

The present disclosure provides novel palladium, rhenium and alumina catalysts that exhibit both high selectivity and high activity in the hydrogenation of aldehydes in chemical compounds containing the aldehyde and other unsaturated bonds, to form an alcohol. These selective catalysts are able to produce commercially valuable materials in high purities and with high efficiency.

I. DEFINITIONS

As used herein, the terms "impregnated" or "impregnate" refer to the technique used to attach ions, atoms or molecules to a solid support, such as incipient wetness impregnation. The technique includes, but is not limited to, attachment via precipitation, diffusion, absorption and adsorption.

As used herein, the terms "adsorbed" or "adsorption" refer to attaching or adhering an atom, ion or molecule to a solid surface in any manner, including but not limited to, ionic or covalent interactions, van der Waals forces, electrostatic attraction, and physisorption and chemisorption.

As used herein, the term "furan-2-carbaldehyde" means a chemical compound with the structure of compound (I) in FIG. 1 and as shown below, containing a furan ring core and an aldehyde moiety at the 2 position of the furan ring. The furan ring may optionally be substituted at one or more of the other positions of the furan ring. In certain embodiments, R, R', and R" are each independently selected from the group consisting of $C_1$-$C_6$ alkyl, $C_1$-$C_6$ alkoxy, halo, COOH, COO—($C_1$-$C_6$ alkyl), ($C_1$-$C_6$ alkyl)-O—($C_1$-$C_6$ alkyl), ($C_1$-$C_6$ alkyl)-COO—($C_1$-$C_6$ alkyl), or ($C_1$-$C_6$ alkyl)-OCO—($C_1$-$C_6$ alkyl). The $C_1$-$C_6$ alkyl group may be linear, branched or cyclic; and may be optionally substituted with halogen, hydroxy or $C_1$-$C_6$ alkoxy. When the furan-2-carbaldehyde is not substituted, that is, when R, R' and R" are all hydrogen, the furan-2-carbaldehyde is furfural. Similarly, when R is —$CH_2OH$, and R' and R" are each hydrogen, the furan-2-carbaldehyde is 5-(hydroxymethyl)furfural.

The structure of compound (I) is:

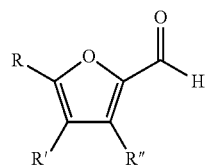

II. CATALYSTS AND METHODS OF MAKING THE CATALYSTS

Catalysts which have shown high selectivity and activity for the hydrogenation of aldehydes may be synthesized by different routes, to provide structurally and functionally distinct entities. These catalysts, however, all contain an alumina support with palladium and rhenium adsorbed thereon. The amount of rhenium in the catalysts is between about between about 4% and about 7% by weight, and the amount of palladium in the catalysts is between about 0.5% and about 5% by weight.

The palladium and rhenium may be absorbed onto the alumina support by dissolution or suspension of a metal salt into a suitable solvent, such as water, and contacting the alumina with the metal salt solution or suspension. The solutions or suspensions may be prepared at a specific pH or within a pH range, as well as at a specific temperature or temperature range. The palladium solution or suspension may be made separately from the rhenium solution or suspension, or a single solution or suspension may be made which contains both palladium and rhenium. In certain embodiments, a solution of palladium is prepared at a pH which is above the isoelectric point of the support. In some embodiments, a solution of palladium is prepared at a pH of between about 9 and about 11. In an embodiment, a solution of palladium is prepared at a pH of about 10. In further embodiments, the temperature that the metal solution or suspension is prepared and/or contacted to the alumina support is ambient (i.e. room) temperature.

The catalysts can be prepared by contacting the metal solution or suspension with the alumina support in order to attach or impregnate the alumina with the metal. If a single solution or suspension is used, containing both the rhenium and the palladium salts, the process is considered to be a co-impregnation. When separate solutions or suspensions are used, the process is considered to be a sequential impregnation of the alumina.

In an embodiment, the catalyst for the hydrogenation of an aldehyde contains an alumina support, rhenium and palladium absorbed to the alumina support, wherein the rhenium is adsorbed to the alumina support before the palladium is adsorbed to the alumina support. In certain embodiments, the catalyst for the hydrogenation of an aldehyde contains an alumina support, rhenium and palladium absorbed to the alumina support, wherein the palladium is adsorbed to the alumina support before the rhenium is adsorbed to the alumina support. In some embodiments, the catalyst for the hydrogenation of an aldehyde contains an alumina support, rhenium and palladium absorbed to the alumina support, wherein the rhenium and the palladium are adsorbed to the alumina support at the same time.

In the instance where a sequential catalyst is prepared and the alumina support initially contacts the rhenium salt solution or suspension, a first composition comprising an alumina support with rhenium absorbed thereto is formed. This composition may be calcined, or may be contacted with a palladium salt solution or suspension to form a second composition. This second composition may be calcined. The method may also include passivation, reduction and/or grinding steps at any appropriate stage of the catalyst preparation. In an embodiment, a first composition comprising an alumina support with rhenium absorbed thereto is calcined prior to its contact with a solution comprising palladium. Calcination may occur at different temperatures. In certain embodiments, the catalyst, first composition or second composition may be calcined at 350° C.; in other embodiments, at 400° C. The length of time the catalyst, first composition or second composition is calcined may also vary. In some embodiments, the calcination time is 1 hour; in other embodiments, it is 3 hours.

The catalysts may also be prepared by contacting the alumina with a solution or suspension of a mixed salt that contains both palladium and rhenium, called a double complex salt, or DCS. The molar ratio of palladium and rhenium in these double complex salts will be fixed depending upon the chemical formula of the salt. In certain embodiments, the double complex salt is $[Pd(NH_3)_4(ReO_4)_2]$, with a Pd:Re ratio of about 1:2.

In an embodiment, a catalyst can be prepared by sequentially contacting a solution comprising rhenium and a solution comprising palladium with the alumina support, or by forming a salt comprising rhenium and palladium, and contacting a solution comprising the salt with the alumina support.

The catalysts can exhibit different structural characteristics and catalytic properties depending upon the method of synthesis and the source of metal used in their formation. The size of the metal particles can vary, as well as their distribution on the alumina support. Tailoring certain structural characteristics of a catalyst can be useful for designing a catalyst with a specific product distribution profile. Catalysts made of palladium and rhenium absorbed onto an alumina support, and which were prepared by a sequential impregnation process as described herein, were found to be superior to the respective monometallic catalysts and conventionally prepared bimetallic catalysts with similar compositions, for the selective hydrogenation of an aldehyde to an alcohol.

Palladium salts which may be used to prepare the catalysts described herein can be any suitable salt, including those with a palladium oxidation state of 0, 1, 2 or 4. In an embodiment, the palladium salt is $Pd(NO_3)_2$. In a further embodiment, the palladium salt is $Pd(NH_3)_4(NO_3)_2$.

Rhenium salts which may be used to prepare the catalysts described herein can be any suitable salt, including those with a rhenium oxidation state of −1, 0, 1, 2, 3, 4, 5, 6, or 7. These salts include perrhenate salts such as sodium and ammonium perrhenates. Halide salts such as $ReCl_6$, $ReCl_5$, $ReCl_3$ and $ReCl_3$ may be suitable, as may bromide and iodide salts, oxyhalide salts such as $ReOCl_4$, and oxides such as $Re_2O_7$. In an embodiment, the rhenium salt is $NH_4ReO_4$. In a further embodiment, the rhenium salt is $HReO_4$.

In some embodiments, the catalysts described herein are prepared with $Pd(NO_3)_2$ and $HReO_4$. In further embodiments, the catalysts described herein are prepared with $Pd(NH_3)_4(NO_3)_2$ and $NH_4ReO_4$. In additional embodiments, the catalysts described herein are prepared with $Pd(NH_3)_4(NO_3)_2$ and $HReO_4$. In some embodiments, more than one type of palladium and/or rhenium salt may be used to prepare the catalyst.

A solid support useful for the catalysts described herein is alumina ($Al_2O_3$), which includes gamma, theta and alpha alumina. In certain embodiments, the solid support is gamma-alumina.

III. METHODS OF USING THE CATALYSTS

The catalysts described herein may be used for methods of hydrogenating chemicals, including those containing an aldehyde moiety in the presence of other sites of unsaturation such as is found in a furan-2-carbaldehyde. In an embodiment, a method of hydrogenating a furan-2-carbaldehyde to a 2-furanmethanol comprises contacting a catalyst comprising rhenium, palladium and an alumina support with the furan-2-carbaldehyde in the presence of hydrogen to provide the 2-furanmethanol.

The catalysts used in these hydrogenation methods may be formed by any of the disclosed methods of preparation. In certain embodiments, the catalyst used for hydrogenation is formed by sequentially contacting a solution comprising rhenium and a solution comprising palladium with the alumina support, or by forming a salt comprising rhenium and palladium, and contacting a solution comprising the salt with the alumina support. In some embodiments, the catalyst was made by sequentially contacting a solution comprising rhenium and a solution comprising palladium with the alumina support, and wherein the alumina support was contacted with the solution comprising rhenium before the solution comprising palladium.

The hydrogenations are performed using catalysts with an amount of rhenium in the catalyst is between about 4% and about 7% by weight, and wherein the amount of palladium in the catalyst is between about 0.5% and about 5% by weight.

In an embodiment, a catalyst used for the hydrogenation of a furan-2-carboxaldehyde was made by sequentially contacting a rhenium solution and a palladium solution with the alumina support, wherein the palladium solution was made with $Pd(NH_3)_4(NO_3)_2$ as the source of palladium. In some embodiments, the catalyst was made by sequentially contacting a rhenium solution and a palladium solution with the alumina support, wherein the solution comprising palladium comprises $Pd(NO_3)_2$ as the source of palladium. In an additional embodiment, the catalyst was made by forming a salt of rhenium and palladium, and contacting a solution comprising the salt with the alumina support. The salt may have a ratio of palladium:rhenium of about 1:2.

The catalysts disclosed here are useful in the selective hydrogenation of aldehydes to form alcohols. The aldehydes which are selectively hydrogenated include furan-2-carboxaldehydes, which contain an unsaturated ring in addition to the aldehyde moiety. In certain embodiments, the catalysts are used for the hydrogenation of a furan-2-carboxaldehyde. In some embodiments, the furan-2-carboxaldehyde is furfural; in other embodiments, the furan-2-carboxaldehyde is 5-(hydroxymethyl)furfural.

Exemplary embodiments of the present disclosure are provided in the following examples. The examples are presented to illustrate the inventions disclosed herein and to assist one of ordinary skill in making and using the same. These are examples and not intended in any way to otherwise limit the scope of the inventions disclosed herein.

IV. EXAMPLES

Two gamma-alumina support materials used in the catalysts described herein are identified by their source, as Grace (G) and Strem (S). The Grace support is Grace-Davison MI-307 having a BET surface area of about 183 $m^2/g$, and the Strem support has a BET surface area of about 217 $m^2/g$. The two supports were characterized by $N_2$ porosimetry and tested for Na, Ca and Mg content by inductively coupled plasma-optical emission spectroscopy (ICP-OES). The Strem support has a lower total pore volume than the Grace support (about 0.47 $cm^3/g$ vs. about 0.77 $cm^3/g$) and higher concentrations of alkali metal impurities, as shown in Table 1, below.

TABLE 1

Characterization of the Grace and Strem alumina supports.

| vendor | BET surface area ($m^2/g$) | Pore volume ($cm^3/g$) | Impurity metal content | |
|---|---|---|---|---|
| | | | Na (ppm) | Ca (ppm) |
| Grace (G) | 183 | 0.77 | <1 | 3.3 |
| Strem (S) | 217 | 0.47 | 316 | 132 |

Example 1

Palladium, Rhenium and Alumina Co-Impregnated Catalysts

Conventional palladium, rhenium and alumina catalysts were prepared by incipient wetness co-impregnation of each support with a single aqueous solution of rhenium and palladium. To achieve a catalyst with a 3 wt % Pd loading, 0.076 g of $Pd(NO_3)_2 \cdot 2H_2O$ (99.9% Pd, Strem) was used per gram of alumina. Similarly, for a catalyst with a 5 wt % Re loading, 0.10 g of a 76.5 wt % solution of $HReO_4$ (99.99% Re, Acros Organics) was used per gram of alumina. Deionized water was used (18 Mohm-cm) for all of the aqueous metal solutions described herein unless stated otherwise. The solution was added slowly to the alumina with intermittent stirring to achieve incipient wetness in a total volume of 1.6 mL solution per gram of alumina.

For the catalyst made with Grace alumina, the resultant paste was dried at 110° C. overnight, crushed and then calcined for 1 h at 350° C. (5° C./min heating rate) in flowing zero-grade air (0.6 L/min, National Welders).

For the catalyst made with Strem alumina, the resultant paste was dried at 110° C. overnight, crushed and then calcined for 3 h at 400° C. (5° C./min heating rate) in flowing zero-grade air (0.6 L/min, National Welders).

The nominal metal loading on each support was 3.0 wt % Pd and 5.2 wt % Re, resulting in an approximate 1:1 Pd:Re atomic ratio for the co-impregnated (co.) bimetallic catalysts. The calcined catalysts were stored in a desiccator prior to use. The palladium precursor $Pd(NH_3)_4(NO_3)_2$ was not useful for formation of a co-impregnated catalyst as it precipitated from the solution in the presence of rhenium under the reaction conditions described above (i.e., formed an insoluble double complex salt).

Example 2

Palladium, Rhenium and Alumina Sequentially-Impregnated Catalysts with Rhenium Impregnated First Re-first sequential palladium, rhenium and alumina catalysts were prepared using two incipient wetness impregnation cycles for each support. First, $Re/Al_2O_3$ was prepared by impregnating Strem alumina with an aqueous solution of $NH_4ReO_4$ (99+%, Alfa Aesar), using 0.08 gram of $NH_4ReO_4$ per gram of alumina, commensurate with about 5 wt % Re loading. Deionized water was used (18 Mohm-cm) for the aqueous metal solutions. The resultant paste was dried overnight at 110° C., then crushed and calcined for 3 h at 400° C. (5° C./min heating rate) in 0.6 L/min zero-grade air (National Welders). This powder was subsequently impregnated with an aqueous solution of $Pd(NH_3)_4(NO_3)_2$ (obtained as a 10 wt % solution from Aldrich, 99% Pd), using 0.619 gm of Pd(NH$_3$)$_4$(NO$_3$)$_2$ per gram of alumina, corresponding to about 3 wt % Pd. The pH of the impregnation solution was adjusted to about 10 using NH$_4$OH (25 wt % NH$_3$, Fisher). The resultant paste was dried overnight at 110° C., then crushed and calcined for 3 h at 400° C. (5° C./min heating rate) in 0.6 L/min zero-grade air (National Welders).

An additional catalyst was prepared as described above using Strem alumina but with each of the two calcining steps performed at 350° C. for 1 h.

Two additional catalysts were prepared as described above using Grace alumina, one with each of the two calcining steps performed at 350° C. for 1 h, and one with each of the two calcining steps performed at 400° C. for 3 h.

The nominal metal loadings for these catalysts were 3.0 wt % Pd and 5.2 wt % Re, resulting in an approximate 1:1 Pd:Re atomic ratio for the bimetallic catalysts. The calcined catalysts were stored in a desiccator prior to use.

An additional Re-first sequential catalyst was prepared using Grace alumina with a nominal loading of 1.5 wt % Pd-5 wt % Re and calcined at 400° C. for 3 h. This catalyst had an approximate 1:2 Pd:Re atomic ratio.

An additional Re-first sequential catalyst was prepared using Strem alumina with Pd(NO$_3$)$_2$.2H$_2$O used as the palladium precursor. The previously described 5 wt % Re/Al$_2$O$_3$ Strem catalyst (calcined at 400° C.) was impregnated with a solution of Pd(NO$_3$)$_2$.2H$_2$O commensurate with 3 wt % Pd loading. The same ratios of precursor:support were used as described above with the Pd(NH$_3$)$_4$(NO$_3$)$_2$ precursor. This was dried overnight, and then calcined at 400° C. for 3 h.

Example 3

Palladium, Rhenium and Alumina Sequentially-Impregnated Catalysts with Palladium Impregnated First Pd-first sequential palladium, rhenium and alumina catalysts were prepared using two incipient wetness impregnation cycles for each support. First, a 3 wt % Pd/Al$_2$O$_3$ catalyst was prepared by incipient wetness impregnation of Grace alumina using an aqueous solution of Pd(NH$_3$)$_4$(NO$_3$)$_2$ (obtained as a 10 wt % solution from Aldrich, 99% Pd), using 0.619 gm of Pd(NH$_3$)$_4$(NO$_3$)$_2$ per gram of alumina, at an approximate pH 10 (adjusted by addition of aqueous NH$_4$OH). Deionized water was used (18 Mohm-cm) for the aqueous metal solutions. This catalyst was dried overnight at 80° C. The resultant powder was crushed, and then calcined at 350° C. for 1 h in 0.6 L/min zero-grade air. It was reduced by heating at 5° C./min in 60 sccm H$_2$ (Research Grade, National Welders) and soaking at 400° C. for 1 h. After cooling in H$_2$ and briefly purging in He at room temperature, air was gradually admitted to the reactor to passivate the catalyst. This catalyst was then impregnated with an aqueous solution of HReO$_4$, using 0.10 g of a 76.5 wt % solution of HReO$_4$ (99.99% Re, Acros Organics) per gram of alumina. The resultant paste was dried overnight at 110° C., crushed, and stored in a desiccator until use.

The nominal metal loading was 3.0 wt % Pd and 5.2 wt % Re, resulting in an approximate 1:1 Pd:Re atomic ratio for the catalyst. After calcination, the catalyst was stored in a desiccator prior to use.

An analogous Pd-first sequential catalyst was prepared using Grace alumina with Pd(NO$_3$)$_2$.2H$_2$O used as the palladium precursor. A Pd/Al$_2$O$_3$ catalyst made from Pd(NO$_3$)$_2$.2H$_2$O was prepared following the procedures described above, was calcined, reduced, passivated and impregnated with a solution of HReO$_4$. The nominal metal loading was 3.0 wt % Pd and 5.2 wt % Re, resulting in an approximate 1:1 Pd:Re atomic ratio for the catalyst. After calcination, the catalyst was stored in a desiccator prior to use.

Example 4

Double Complex Salt (DCS) Catalysts

A double complex salt (DCS), [Pd(NH$_3$)$_4$(ReO$_4$)$_2$], was prepared by mixing saturated aqueous solutions of NH$_4$ReO$_4$ and Pd(NH$_3$)$_4$(NO$_3$)$_2$ at 25° C. The concentration of the Pd(NH$_3$)$_4$(NO$_3$)$_2$ solution was about 4.5 mM, and the concentration of the NH$_4$ReO$_4$ solution was about 0.23 M. Upon mixing, a light yellow salt precipitated from solution; the precipitate was filtered, washed thoroughly with deionized (DI) H$_2$O, and dried at room temperature. The catalyst was prepared by wet impregnation of the Grace alumina support with the DCS at a loading of 1.5 wt % Pd, 5.2 wt % Re, resulting in an approximate molar ratio of 1:2 Pd:Re, fixed by the composition of the DCS. Due to the relative insolubility of the DCS in the solvents tested (water, acetone, ethanol, ethyl acetate, and acetonitrile), impregnation was carried out using an aqueous solution with a ratio of 10 mL/g support at 80° C. A rotary evaporator with a bath temperature of 80° C. was used to warm the alumina support and keep the DCS dissolved. Water was evaporated slowly under reduced pressure. When the catalyst appeared dry, it was removed and further dried at 110° C. in air overnight. The dried DCS catalyst was used without calcination unless otherwise noted. A fraction of the DCS catalyst was calcined at 350° C. for 1 h in 0.6 L/min zero-grade air.

Example 5

Comparative Palladium-Only Alumina Catalysts

A 3 wt % Pd/Al$_2$O$_3$ catalyst was prepared by incipient wetness impregnation of Grace alumina using a solution of 0.619 g Pd(NH$_3$)$_4$(NO$_3$)$_2$ per gram of Al$_2$O$_3$ support in de-ionized water at an approximate pH 10 (adjusted by addition of aqueous NH$_4$OH). This catalyst was dried overnight at 80° C. The resultant powder was crushed, and then calcined at 350° C. for 1 h in 0.6 L/min zero-grade air (0.6 L/min, National Welders).

An additional 3 wt % Pd/Al$_2$O$_3$ catalyst was prepared by incipient wetness impregnation of Grace alumina using a solution of 0.076 g Pd(NO$_3$)$_2$—H$_2$O per gram of Al$_2$O$_3$ support in de-ionized water at neutral pH. This catalyst was dried overnight at 80° C. The resultant powder was crushed, and then calcined at 350° C. for 1 h in 0.6 L/min zero-grade air (0.6 L/min, National Welders).

An additional catalyst was prepared with a 1.5 wt % nominal palladium loading using Pd(NH$_3$)$_4$(NO$_3$)$_2$ and Grace alumina in the same manner as described above for the 3 wt % Pd-only catalyst, with the amount of palladium adjusted appropriately to reflect the lower loading level.

Example 6

Comparative Rhenium-Only Alumina Catalysts

A comparative Re/Al$_2$O$_3$ catalyst was prepared by impregnating Grace alumina with a solution of 0.080 g $NH_4ReO_4$ per gram of alumina in de-ionized water, commensurate with about 5 wt % rhenium loading. The resultant paste was dried overnight at 110° C., then crushed and calcined for 3 h at 400° C. (5° C./min heating rate) in 0.6 L/min zero-grade air (National Welders).

A second $Re/Al_2O_3$ catalyst was prepared by impregnating Grace alumina with a solution of 0.100 g $HReO_4$ solution per gram of alumina in de-ionized water, commensurate with about 5 wt % rhenium loading. The resultant paste was dried overnight at 110° C., then crushed and calcined for 3 h at 400° C. (5° C./min heating rate) in 0.6 L/min zero-grade air (National Welders).

Catalyst Characterization

Effect of Palladium Salt Used to Prepare Catalysts.

Catalysts prepared using $Pd(NH_3)_4(NO_3)_2$ as the palladium source were referred to as "Pd tetraammine" (or "Pd TA") catalysts, and those prepared using $Pd(NO_3)_2 \cdot 2H_2O$ as the palladium source were referred to as "Pd nitrate" (or "Pd $NO_3$") catalysts. It was found that palladium-only alumina catalysts which were prepared with Pd tetraammine contained smaller particles of palladium, i.e. the palladium was more highly dispersed, when compared to the palladium particles shown in the catalyst prepared using Pd nitrate.

Figure 2:
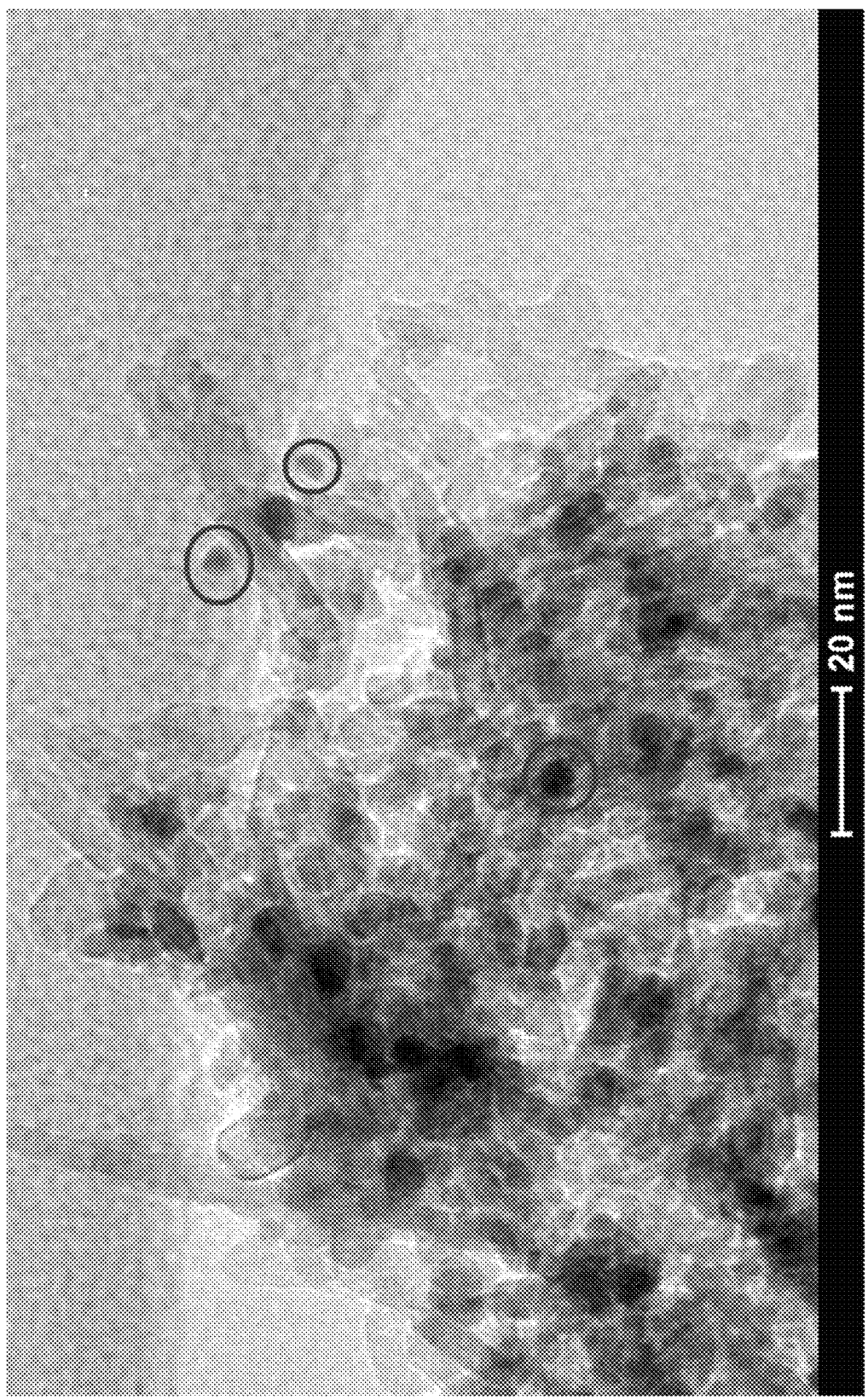
FIG. 2 is a transmission electron microscopy (TEM) image of an exemplary catalyst using $Pd(NO_3)_2$ as the source of palladium.
Figure 3:
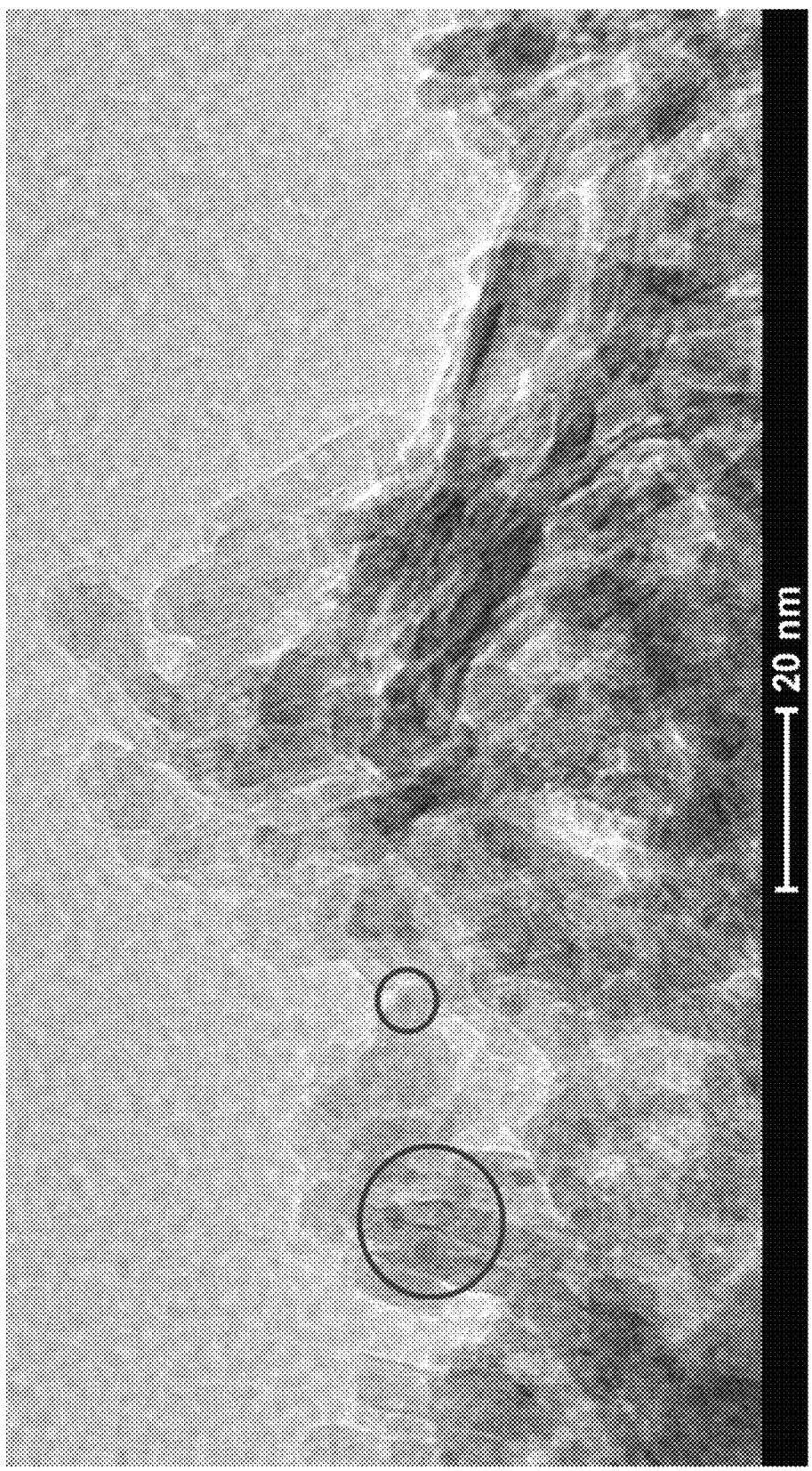
FIG. 3 is a TEM image of an exemplary catalyst using $Pd(NH_3)_4(NO_3)_2$ as the source of palladium.

FIG. 2 is a bright-field transmission electron microscopy (TEM) image of a palladium on alumina catalyst prepared using Grace alumina and $Pd(NO_3)_2$, or Pd nitrate, as the source of palladium. FIG. 3 is a bright-field TEM image of a palladium on alumina catalyst using Grace alumina and $Pd(NH_3)_4(NO_3)_2$, or Pd tetraammine, as the source of palladium.

The TEM images show the difference in particle size between the palladium on alumina catalysts prepared using Grace alumina and the Pd nitrate (FIG. 2) and Pd TA (FIG. 3) precursors. Particles >4 nm in diameter are evident in FIG. 2, whereas most particles in FIG. 3 have diameters of 2 nm or less, consistent with CO chemisorption results for these two catalysts (discussed in more detail below). Without being bound by theory, this suggests that employing a solution of a cationic metal precursor having a pH greater than the isoelectric point of the alumina support, as with Pd tetraammine, leads to smaller metal particles adsorbed on the alumina support.

Figure 4A:
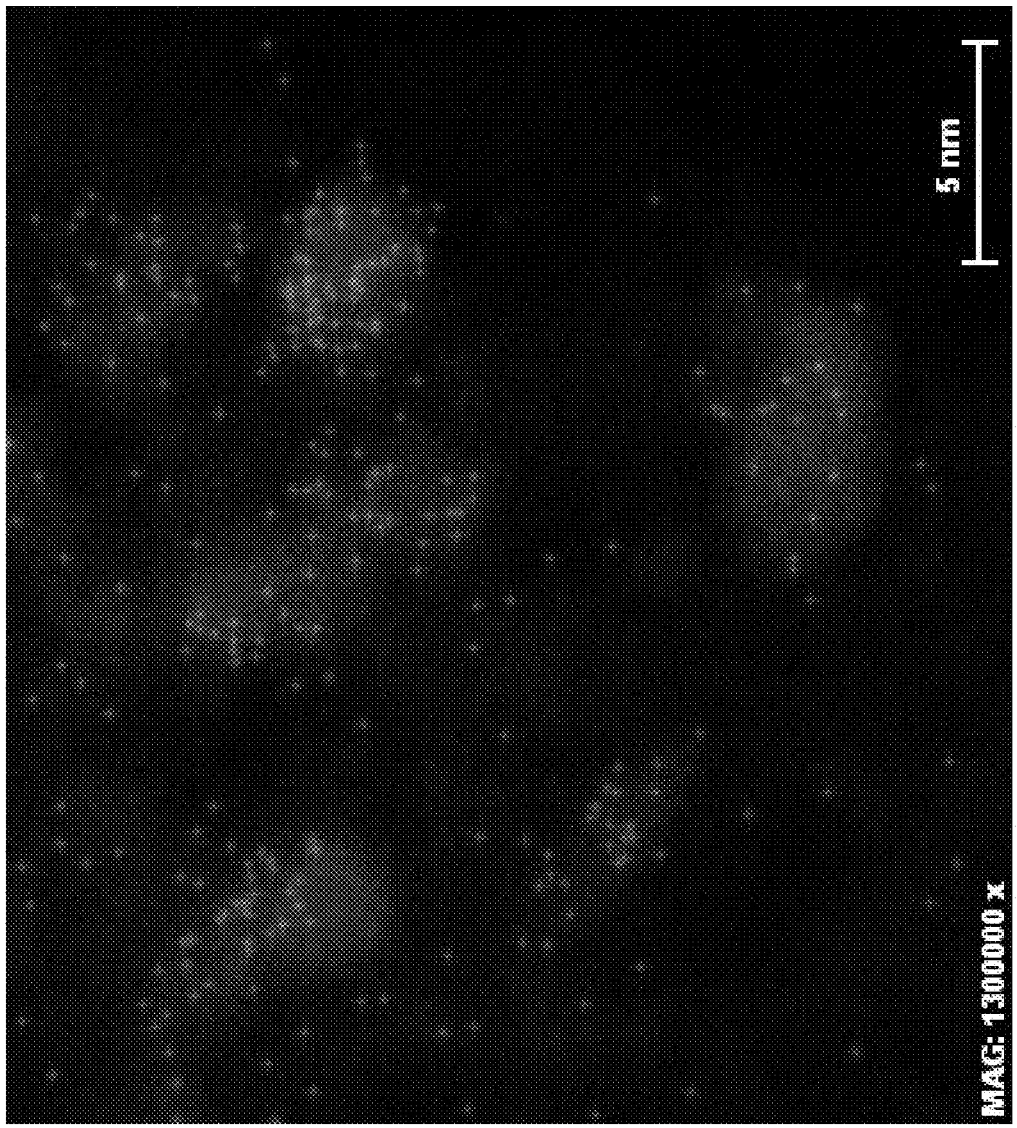
FIGS. 4(a)-4(c) show TEM images of additional exemplary catalysts made with various metal sources.
Figure 4B:
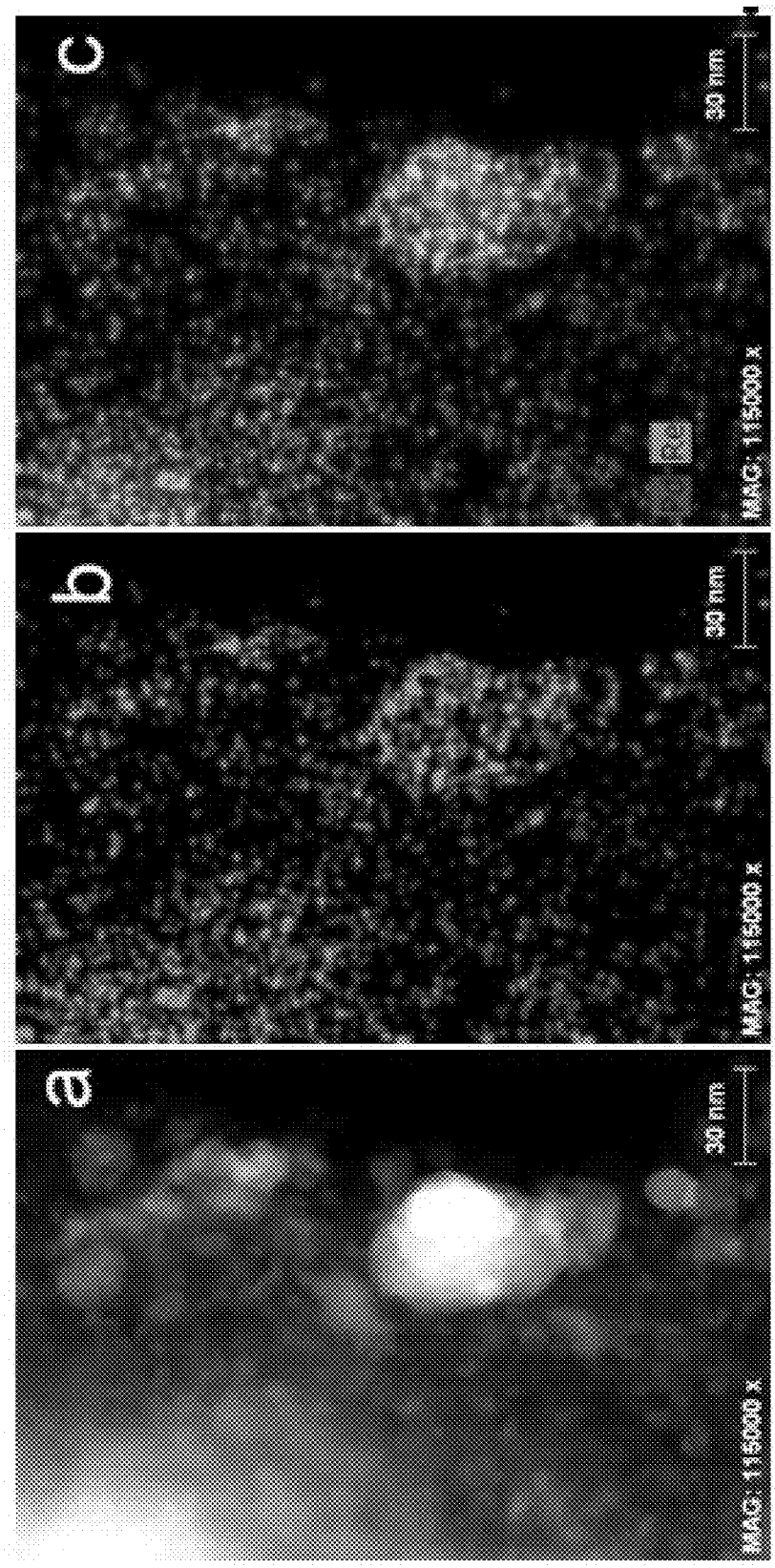
Figure 4C:
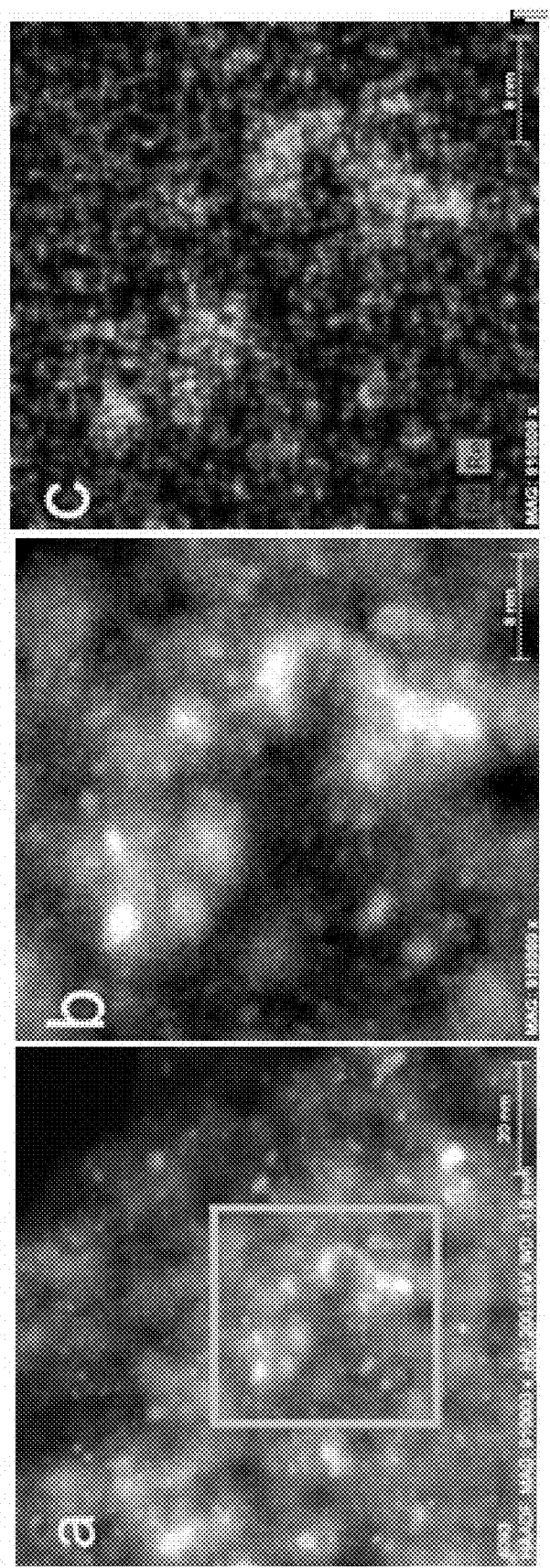

FIGS. 4(a)-(c) are TEM images of rhenium-containing catalysts using Strem alumina, which exhibited high selectivity in the production of furfural alcohol in the hydrogenation of furfural (discussed in more detail below).

FIG. 4(a) is a high-angle annular dark field (HAADF) STEM image with an energy-dispersive x-ray (EDX) analysis map overlay of an Re-first catalyst made with Pd TA as the palladium precursor, showing bright objects as a grouping of several 4-5 nm supported metal particles. Overlaying the TEM image is an energy-dispersive x-ray (EDX) analysis map of Pd (green) and Re (blue) species in the same analysis region. Substantial overlap of the green and blue species which make up the particles is shown, providing evidence of bimetallic nanoparticles in this catalyst.

FIG. 4(b) is a similar HAADF STEM image (in panel a) with an energy-dispersive x-ray (EDX) analysis map overlay of rhenium (in panel b), and a composite overlay (in panel c) of a Pd-first catalyst made with Pd nitrate as the palladium precursor. The energy-dispersive x-ray (EDX) analysis map shows Re (green), and the composite overly shows Pd (red) and Re (green) species. Again, substantial overlap of the green and red species which make up the particles is shown, providing evidence of bimetallic nanoparticles in this catalyst. The rhenium particles are shown in panel b in green, with the palladium particles added in panel c in red. The approximate sizes of the metal particles are evident, as well.

FIG. 4(c) is a HAADF-STEM image (in panel a), a HAADF-STEM image (in panel b), and a STEM-EDX analysis map overlay (in panel c) of a Re-first catalyst made with Pd nitrate as the palladium precursor. The EDX analysis map shows Re (green) and Pd (red) species. Substantial overlap of the green and red species which make up the particles is shown, providing evidence of bimetallic nanoparticles in this catalyst. The approximate sizes of the metal particles are evident, as well.

CO Chemisorption.

Tables 2a, 2b and 3 provide the nominal metal loadings and CO chemisorption results for catalysts formed using Grace and Strem alumina supports, respectively. Dispersions are reported on Pd-only and total metals (i.e. Pd+Re) bases, and generally indicate how completely the metal is distributed on the alumina surface. The dispersion value is the ratio of surface metal atoms to total metal atoms. Since only surface atoms are active, provides an understanding of how efficiently the metal loaded on the catalyst is for the hydrogenation. A higher dispersion percentage corresponds to more metal surface area per gram of total metal loaded on the support. Thus, a catalyst with a higher dispersion percentage has more active metal particles present on the support than a catalyst with a lower dispersion percentage.

In Tables 2a, 2b and 3, the sequential catalysts listed are all rhenium-first sequential catalysts prepared using Pd TA as the palladium precursor, with the ratio of Pd:Re as indicated. The bimetallic co-impregnated catalyst listed was made with Pd nitrate as the palladium precursor. The Pd-only and Re-only catalysts are made with the indicated metal precursors.

TABLE 2a

Catalyst preparation and metal content by ICP-OES on Grace alumina

| Catalyst | Metal precursors | Pd loading (wt %) | Re loading (wt %) | Calcination conditions |
| --- | --- | --- | --- | --- |
| Pd ($NO_3$) | $Pd(NO_3)_2$ | 3.04 | — | 350° C., 1 h |
| Pd (TA) | $Pd(NH_3)_4(NO_3)_2$ | 3.00 | — | 350° C., 1 h |
| PdRe co. | $Pd(NO_3)_2$ and $HReO_4$ | 3.02 | 5.00 | 350° C., 1 h |
| Re on Pd | $Pd(NO_3)_2$ and $HReO_4$ | 2.53 | 4.92 | 350° C., 1 h |
| PdRe seq. (350) | $NH_4ReO_4$ and $Pd(NH_3)_4(NO_3)_2$ | 2.84 | 4.55 | 350° C., 1 h |
| PdRe seq. (400) | $NH_4ReO_4$ and $Pd(NH_3)_4(NO_3)_2$ | 2.98 | 4.85 | 400° C., 3 h |
| PdRe (1:2) seq. | $NH_4ReO_4$ and $Pd(NH_3)_4(NO_3)_2$ | 3.02 | 9.21 | 350° C., 1 h |
| 5% Re (H) | $HReO_4$ | — | 6.08 | 350° C., 1 h |
| 10% Re (H) | $HReO_4$ | — | 9.61 | 350° C., 1 h |
| Re (N) | $NH_4ReO_4$ | — | 5.02 | 400° C., 3 h |

TABLE 2b

Additional data for Grace (G) Catalysts

| Catalyst | Pd (wt. %) | Re (wt. %) | Metals basis | Pd basis |
| --- | --- | --- | --- | --- |
| Pd-nitrate** | 2.9* | 0 | 15 | 15 |
| Pd-tetraammine** | 3 | 0 | 56 | 56 |
| PdRe (1:1) seq | 3 | 5.3 | 19 | 47 |
| PdRe (1:2) seq | 3 | 10 | 14 | 51 |
| PdRe co | 3 | 5.3 | 10 | 24 |
| Re-$HReO_4$** | 0 | 5.3 | 10 | — |

*measured by ICP-OES;
**indicates metal precursor

TABLE 3

Catalysts supported on Strem alumina (S)

| Catalyst | Pd (wt. %) | Re (wt. %) | Dispersion (%) Metals basis | Dispersion (%) Pd basis |
|---|---|---|---|---|
| Pd-tetraammine | 3 | 0 | 55 | 55 |
| PdRe (1:1) seq | 3 | 5.3 | 22 | 53 |
| PdRe co | 3 | 5.3 | 13 | 31 |
| Re-HReO$_4$** | 0 | 5.3 | 7.4 | — |
| Re-NH$_4$ReO$_4$** | 0 | 5.3 | 7.2 | — |

**indicates metal precursor

Lower metal dispersions are obtained for the bimetallic samples when based on the combined Pd+Re content (i.e. total metals basis). Rhenium-only catalysts exhibit Re dispersion values of 10% or less, which indicates that not much CO was absorbed. Based on the TEM/EDX data, the rhenium particles in these catalysts are not larger than about 2-3 nm. The TEM/EDX data suggests that the dispersion of Re should be about ~50% dispersion, using an approximate correlation of dispersion being equal to 1/average diameter in units of nm. Thus, a 10% dispersion should result from 10 nm particles, and not from the smaller rhenium particles indicated by TEM/EDX. Thus, a more accurate measure of dispersion may be that obtained using the Pd-only basis.

Palladium-only and sequential palladium-rhenium catalysts prepared with Pd tetraammine have similar dispersions using a Pd-only basis, indicating small Pd particles. Metal particles are larger in the palladium-rhenium catalysts prepared by sequential impregnation made with Pd nitrate as the palladium precursor, than with Pd TA as the palladium precursor, as shown by the TEM data.

CO Diffuse Reflectance Infrared Fourier Transform Spectroscopy (DRIFTS).

Figure 5A:
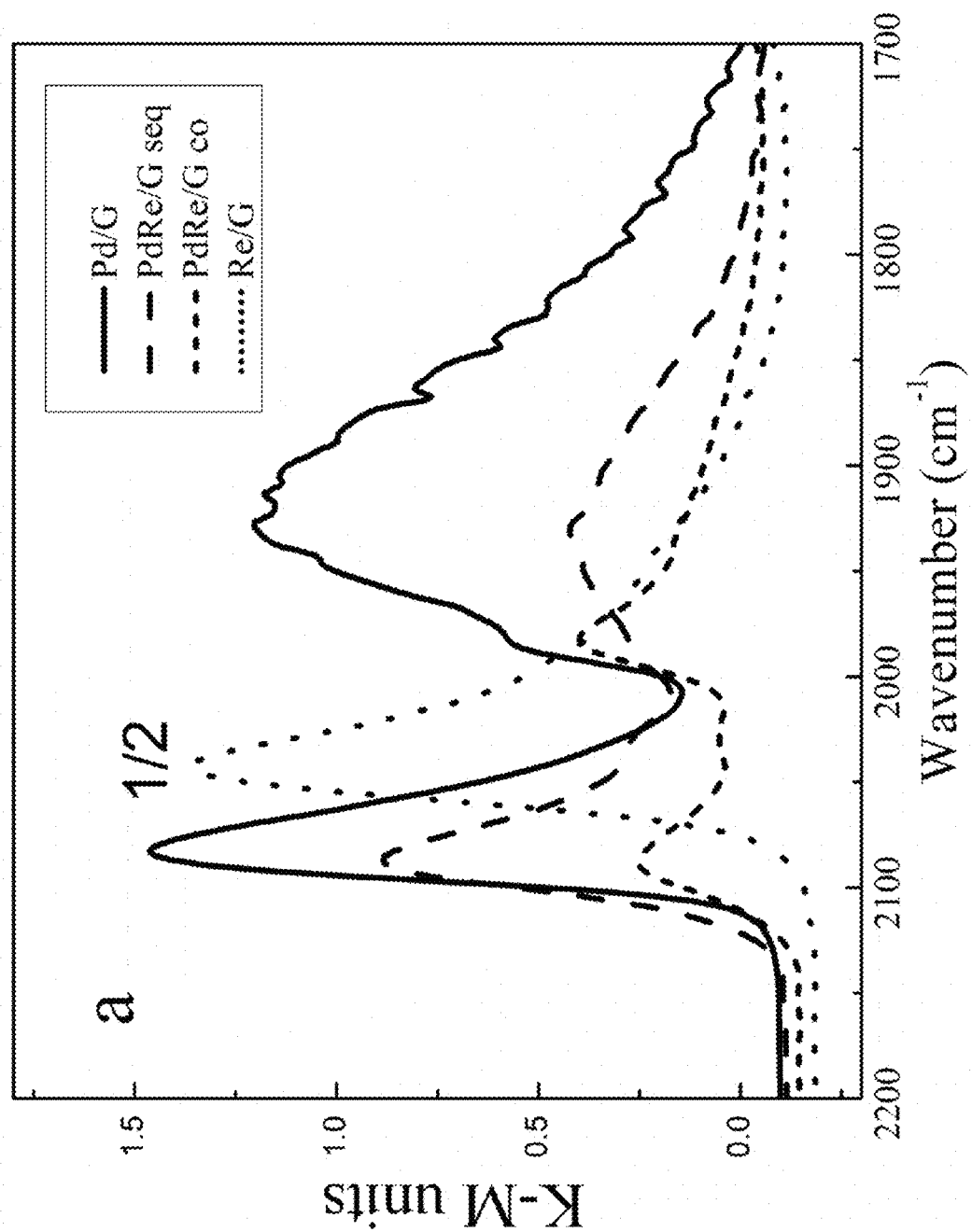
FIGS. 5(a)-5(b) show infrared (IR) spectra of adsorbed carbon monoxide (CO) obtained using diffuse reflectance IR Fourier transform spectroscopy (DRIFTS) from exemplary catalysts.
Figure 5B:
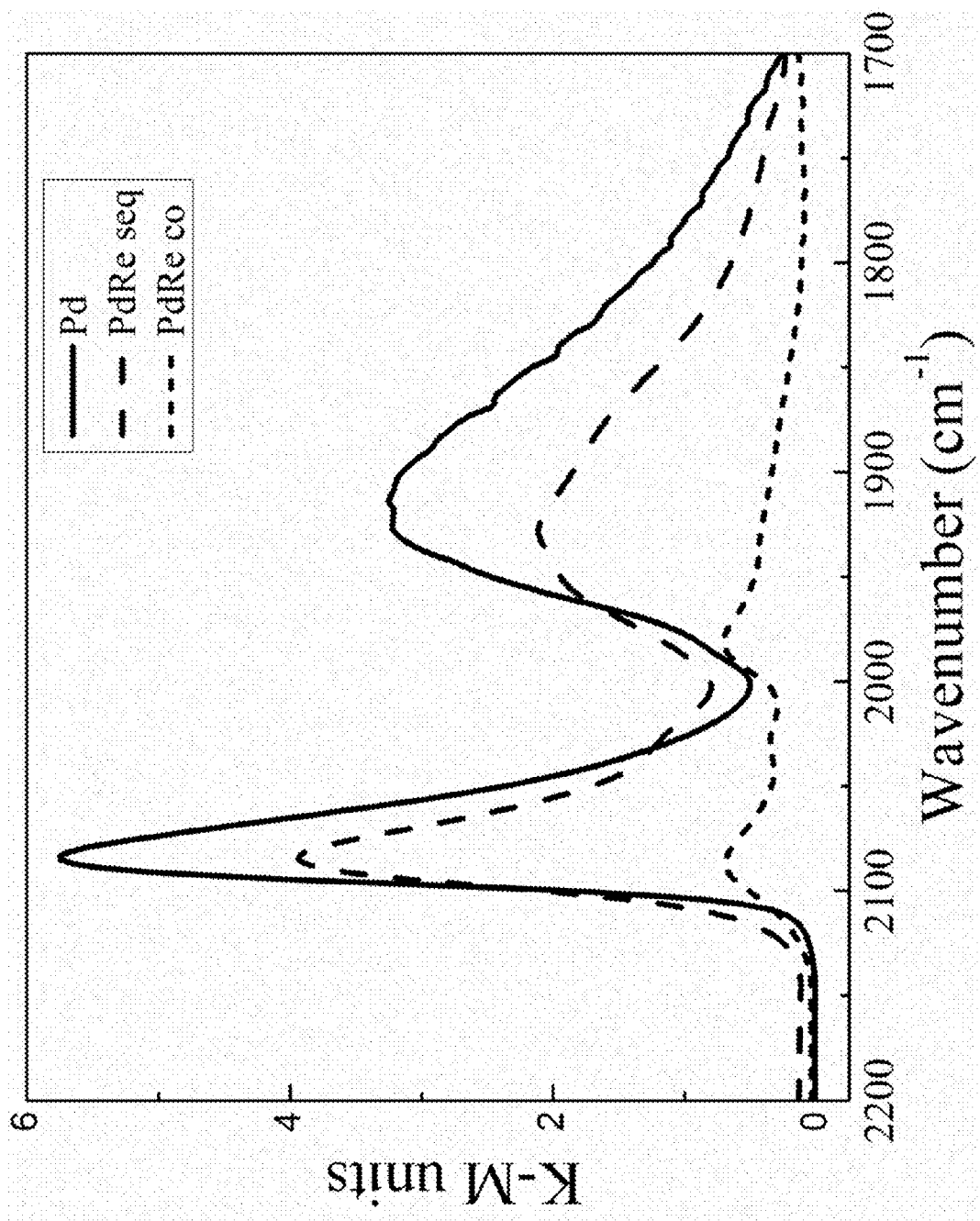

FIGS. 5(a)-5(b) show infrared (IR) spectra of adsorbed carbon monoxide (CO) obtained using DRIFTS from a series of catalysts. FIG. 5(a) is spectra from catalysts made with Grace alumina, and FIG. 5(b) is spectra from catalysts made with Strem alumina.

DRIFT spectra were measured on a Bruker Vertex 70 FTIR using a Harrick Praying Mantis cell with a high temperature in situ DRIFTS cell. After reduction at 400° C. for 1 h in 40 sccm H$_2$ (research, National Welders), catalysts were purged in He at 40 sccm (UHP, National Welders) for 1 h before cooling to 20° C. Pulses of 5% CO/He (certified, National Welders) were administered five at a time at 20° C. until no further changes in spectra were observed.

Three distinct νCO bands at ~2090, 1980 and ~1920 cm$^{-1}$ due to linear (atop) CO, bridging CO on facets of larger Pd particles, e.g., (111), (110), and triply bridging CO, respectively, are observed for each catalyst. In the bimetallic catalysts, a fourth νCO band at ~2040 cm$^{-1}$ is assigned to linearly adsorbed (atop) CO on rhenium. The νCO spectral intensities are in reasonable agreement with the CO chemisorption results. The relative intensities of linear and bridging bands in each spectrum correlate with particle size; a higher linear-to-bridge (L-B) ratio typically indicates small particles. As noted above, TEM images and the CO chemisorption results show 2-4 nm particles present in palladium on Grace alumina catalysts prepared from the Pd tetraammine precursor.

The L-B ratio is larger for the palladium on Strem alumina catalysts and the sequentially-impregnated bimetallic catalysts on Strem alumina. In contrast, the co-impregnated bimetallic catalysts made with Pd nitrate contain larger Pd particles, as evidenced by their low-intensity νCO spectra and lower L-B ratios. This is shown by comparing the bands for the linear CO on Pd at ~2080 cm$^{-1}$ to the bands for the bridging CO at ~1930 cm$^{-1}$ in the case of Pd(TA) catalysts. The 1930 cm$^{-1}$ peak corresponds to CO on Pd(111) planes. The Pd nitrate catalysts have the same linear CO peak, but the bridging CO on Pd is at 1990 cm$^{-1}$ which is CO on Pd(100) planes, which are preferentially exposed on larger Pd particles.

Temperature-Programmed Reduction (TPR) and Temperature-Programmed Hydride Decomposition (TPHD).

Figure 6A:
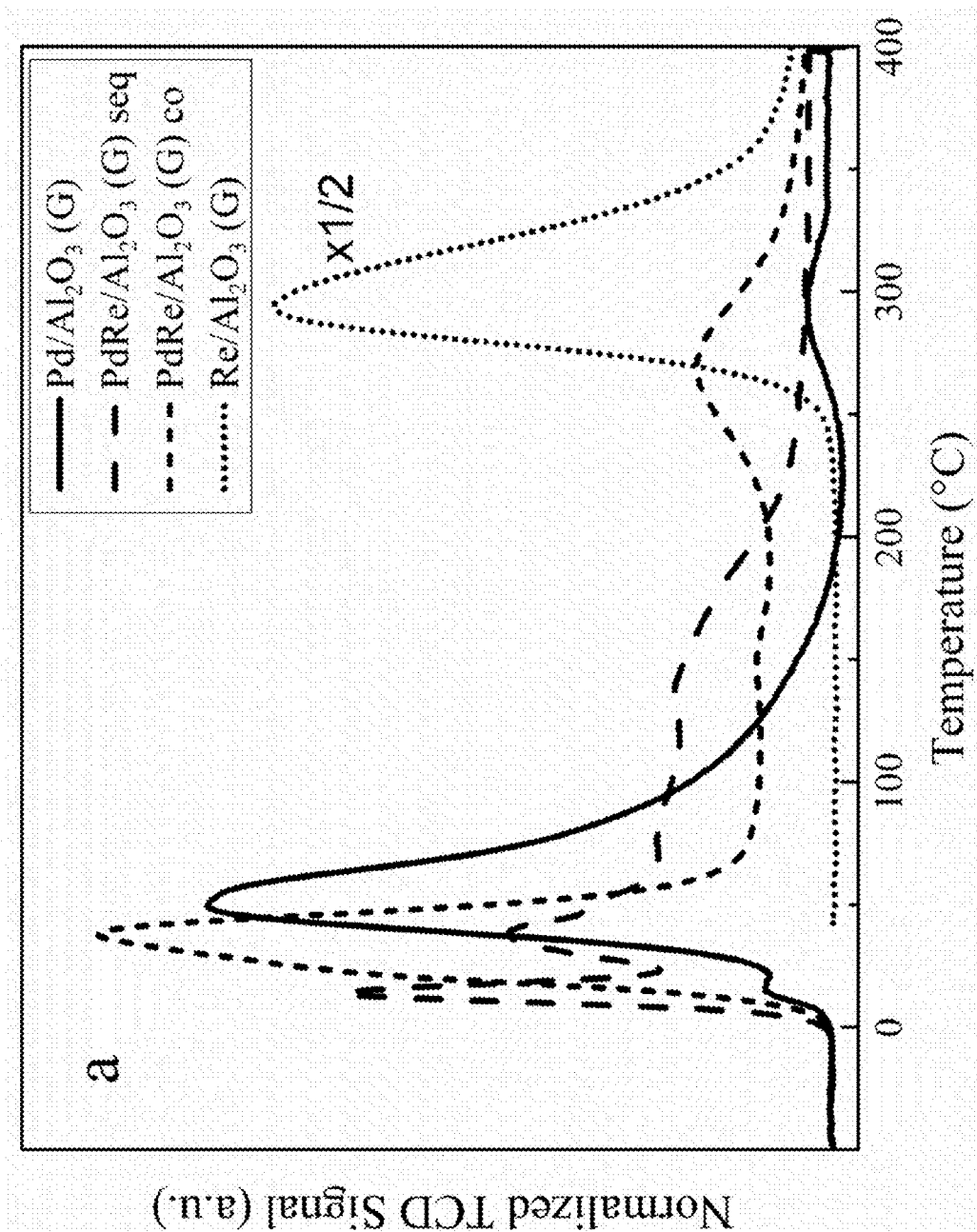
FIGS. 6(a)-(b) show temperature-programmed reduction (TPR) profiles obtained from exemplary catalysts.
Figure 6B:
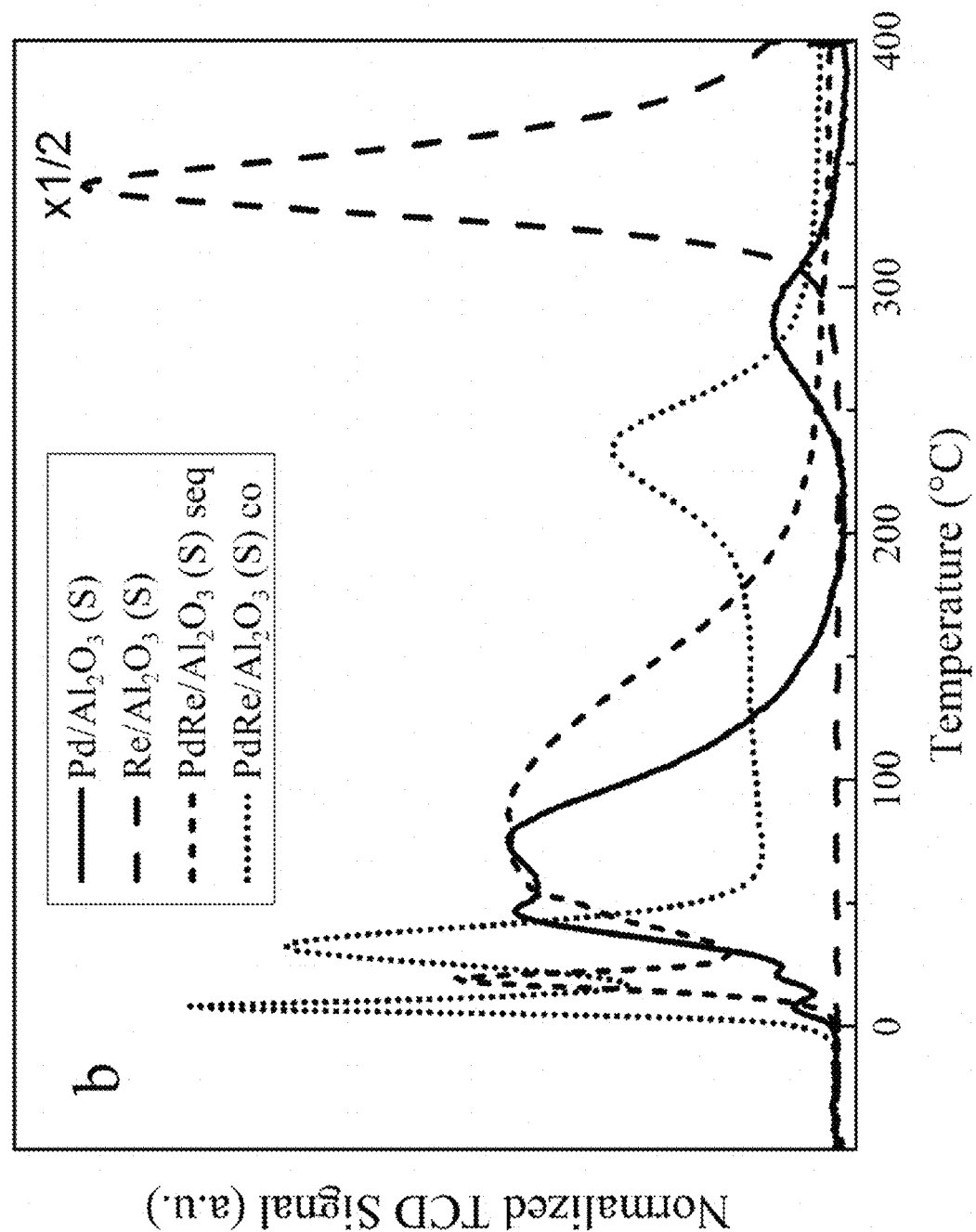

FIG. 6(a) shows temperature-programmed reduction (TPR) profiles obtained from a series of catalysts made with Grace alumina, and FIG. 6(b) shows profiles obtained from a series of catalysts made with Strem alumina.

Monometallic palladium on alumina catalysts prepared using the Pd TA precursor exhibit similar Pd reduction profiles, as shown in the TPR profiles in FIGS. 6(a)-(b). In these figures, the Pd-only catalysts use Pd TA, the co-impregnated catalysts used Pd nitrate, and the sequential catalysts are all Re-first sequential catalysts using Pd TA as the palladium precursor.

The monometallic palladium on Strem alumina catalyst analyzed in FIG. 6(b) shows a significant TPR peak at 300° C., which is well above the palladium reduction temperature. This peak is associated with alkali impurities in the alumina that form carbonates, which decompose in H$_2$ yielding methane. The TPR profiles indicate that most of the rhenium in the bimetallic catalysts is reduced at lower temperatures than for the monometallic 5 wt % rhenium on alumina catalyst (see the green curves in FIGS. 6(a)-(b)), suggesting either mobility of rhenium oxide species or close proximity of the rhenium with the palladium, facilitating hydrogen spillover from the palladium particles. On both the Grace and Strem supports, the co-impregnated bimetallic catalyst has a distinct TPR feature at ~250° C., likely due to segregated rhenium oxide species, whereas the hydrogen uptake drops off above 150° C. in the TPR profiles of the sequentially impregnated catalysts.

Figure 7:
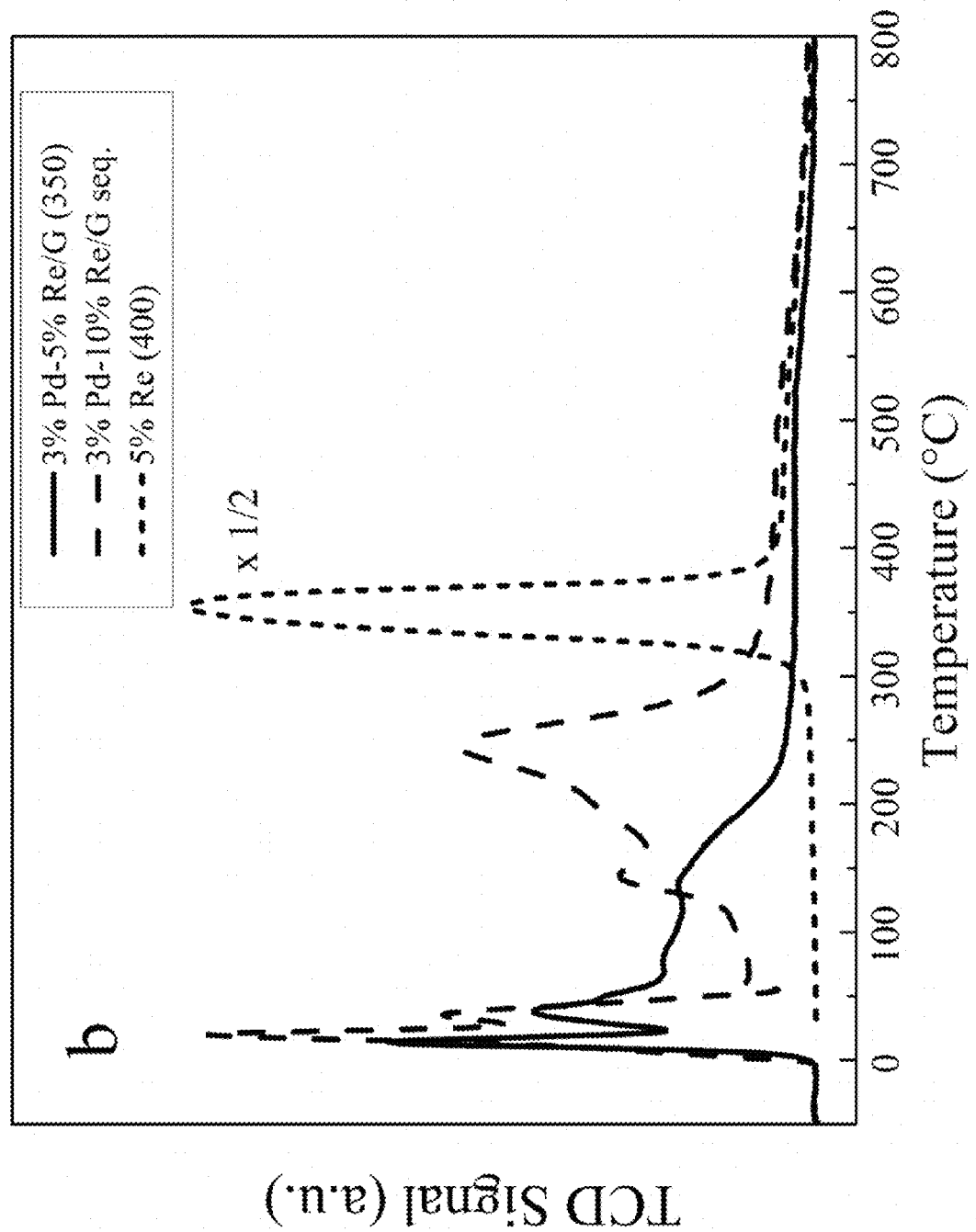
FIG. 7 shows TPR profiles obtained from additional exemplary catalysts made with Grace alumina.

When the rhenium loading is increased, as in the bimetallic sequentially-impregnated catalysts with a nominal rhenium loading of 5 wt % and 10 wt %, on Grace alumina (i.e. comparing the PdRe (1:2) and PdRe (1:1) catalysts), a high-temperature TPR feature at ~250° C. appears (see FIG. 7). This feature is consistent with the reduction of rhenium oxide species. For comparison, a monometallic catalyst with a 5 wt % rhenium loading on Grace alumina is shown.

In FIG. 7, the sequential catalysts are all Re-first sequential catalysts using Pd TA as the palladium precursor and the indicated amount of rhenium. As shown, the rhenium is reduced at a much lower temperature when palladium is present than in the Re-only catalyst.

Figure 8A:
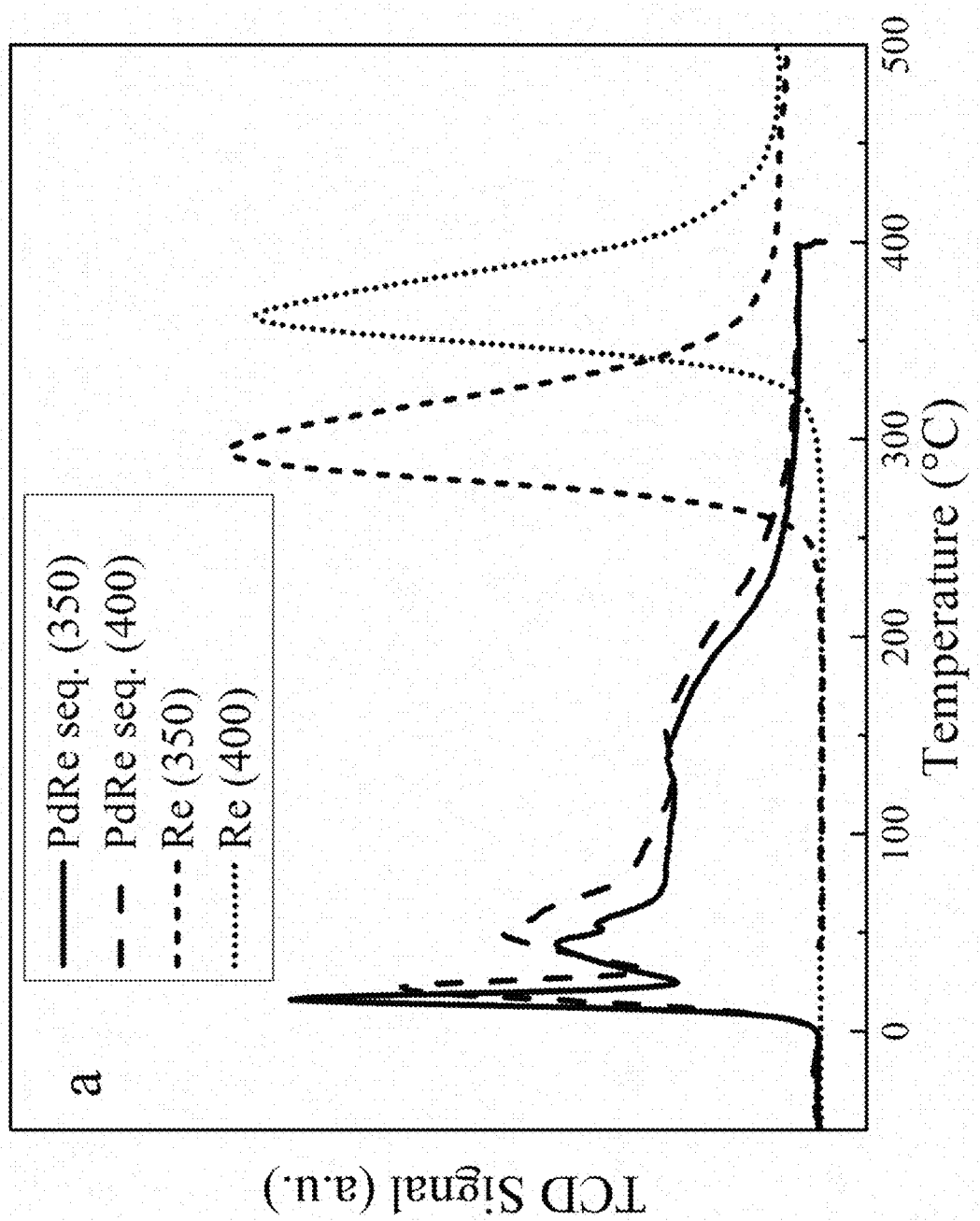
FIGS. 8(a)-(b) show TPR profiles obtained from additional exemplary catalysts.
Figure 8B:
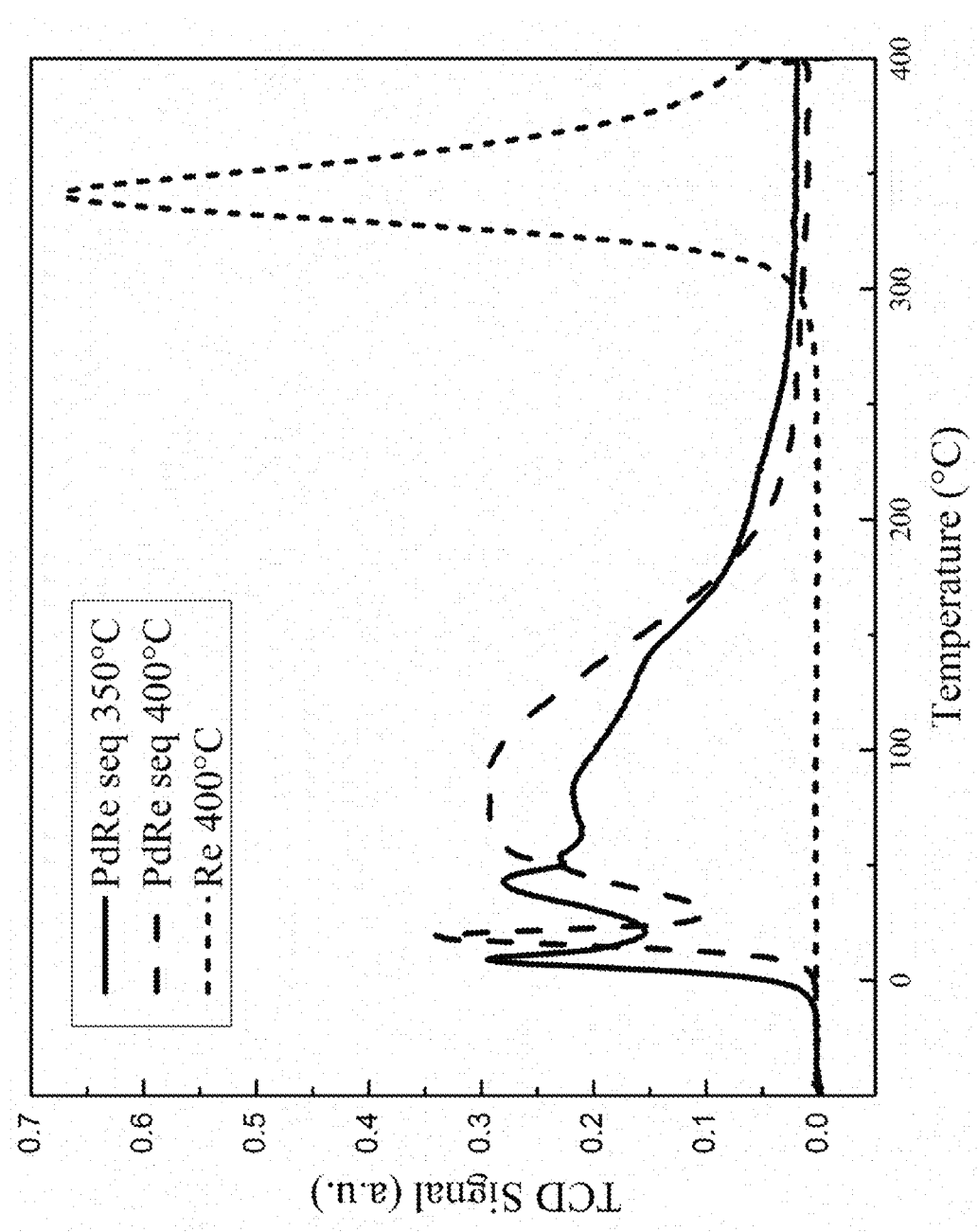

The effect of the calcination temperature was also studied. FIG. 8(a) shows the TPR profiles obtained from a series of catalysts made with Grace alumina, and FIG. 8(b) shows the TPR profiles obtained from a series of catalysts made with Strem alumina, with calcination performed at either 350° C. or 400° C. In these figures, the sequential catalysts are all Re-first sequential catalysts made using Pd TA as the palladium precursor.

TPR profiles of the sequentially-impregnated bimetallic catalysts show a shift in the reduction features to higher temperature with increasing calcination temperature. Quantitative results obtained by temperature-programmed hydride decomposition (TPHD) studies (discussed in more detail below) demonstrate an increase in the average rhenium oxidation state after treatment in H$_2$ at 400° C. for 1 h.

This suggests that oxidic rhenium species (ReO$_x$) in contact with palladium particles are possible active sites for selective hydrogenation.

Figure 9A:
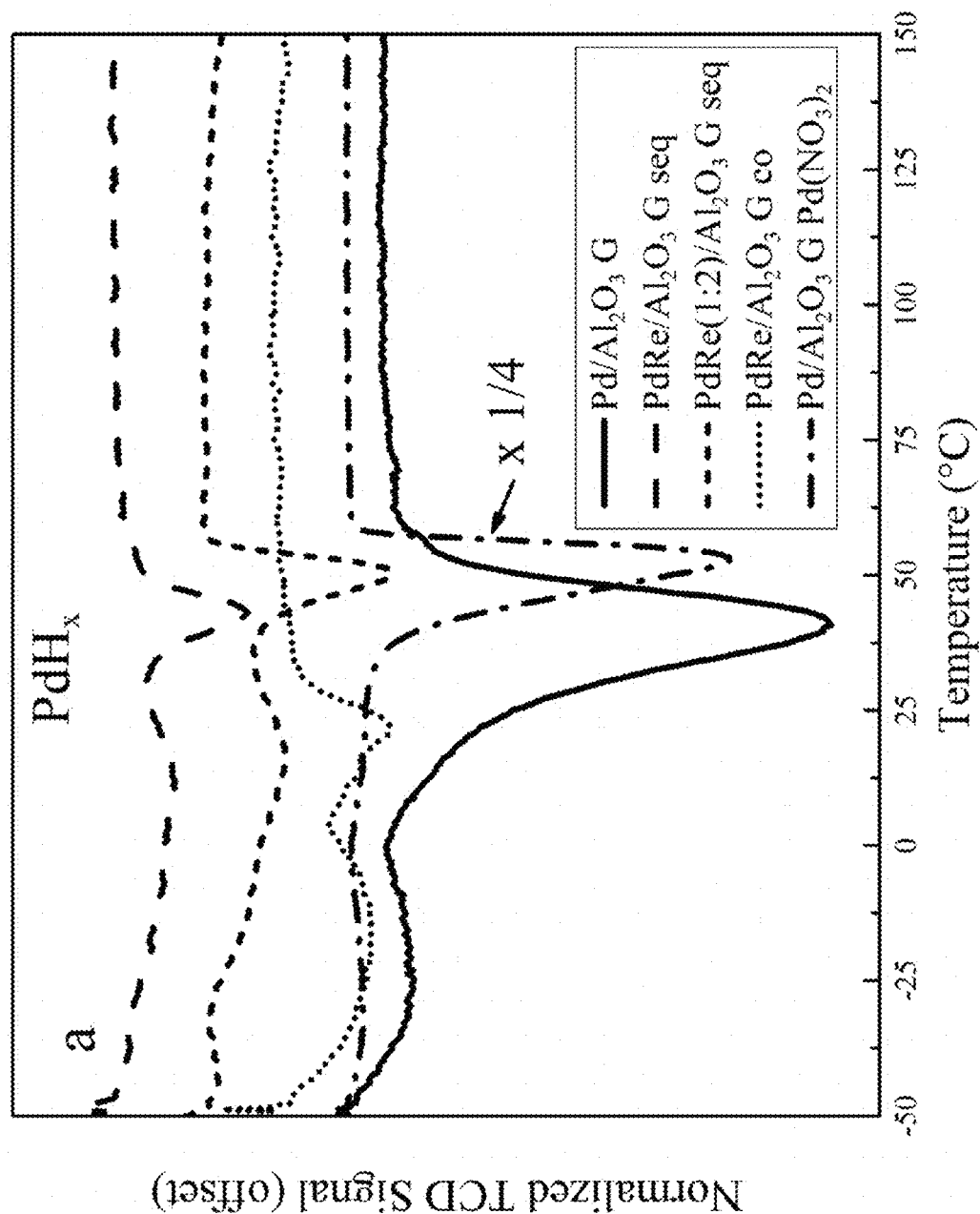
FIGS. 9(a)-(b) show the temperature-programmed hydride decomposition (TPHD) profiles obtained from exemplary catalysts.
Figure 9B:
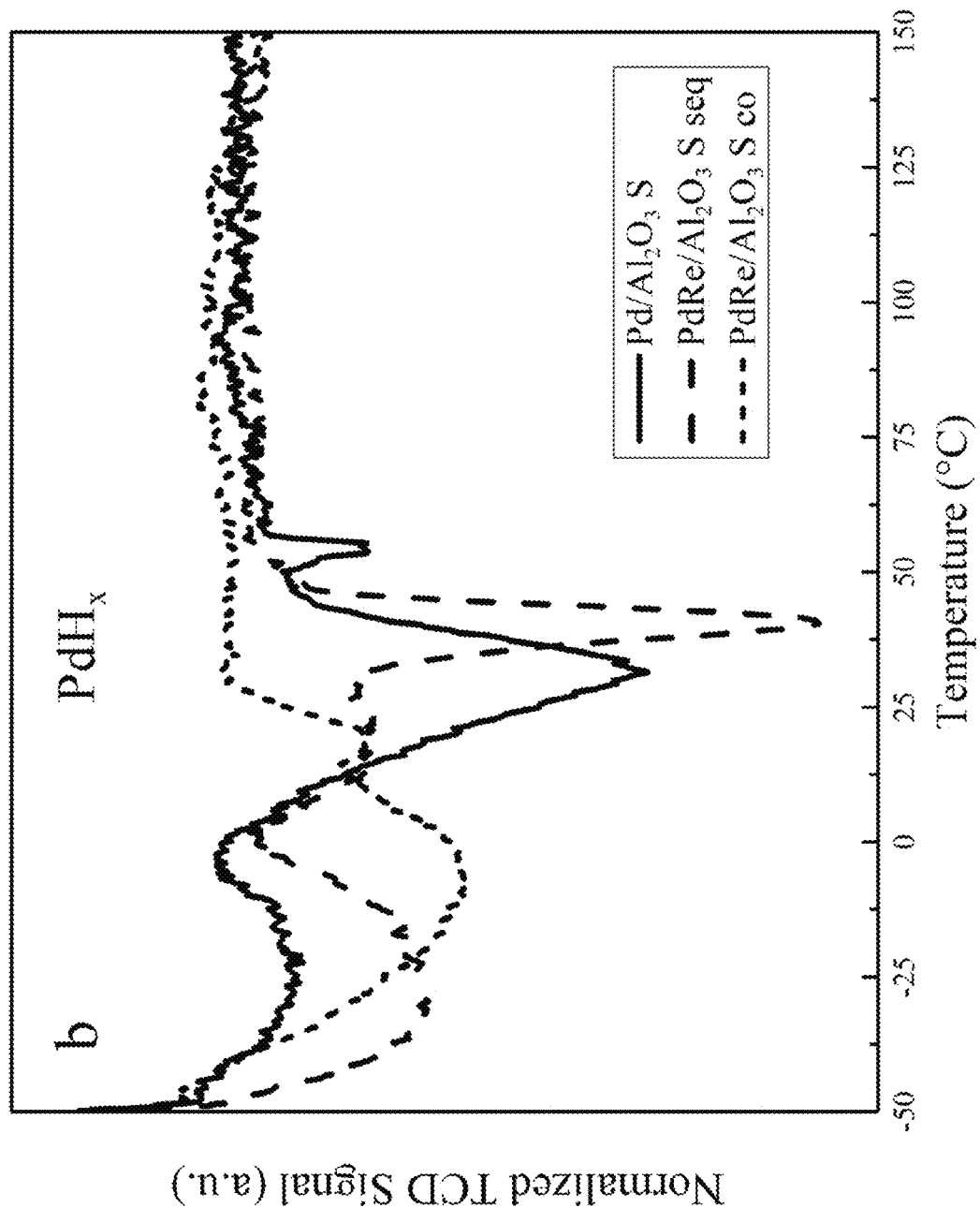

Temperature-programmed hydride decomposition (TPHD) profiles of a series of catalysts prepared with Pd TA show suppression of hydride formation when compared to catalysts prepared with Pd nitrate. FIG. 9(a) show the TPHD profiles obtained from catalysts made with Grace alumina, and FIG. 9(b) show the TPHD profiles from catalysts made with Strem alumina, under an atmosphere of 5% H$_2$/Ar. The H/Pd values are given in Table 4. The H/Pd ratio for the bulk PdH$_x$ phase is 0.65-0.70. For these catalysts, the Pd-only catalysts use Pd TA unless labeled otherwise, the co-impregnated catalysts used Pd nitrate, and the sequential catalysts are all Re-first sequential catalysts using Pd TA as the palladium precursor with a ratio of Pd:Re being 1:1 unless labeled otherwise.

For the data shown in Table 4, TPHD experiments were performed using a Micromeritics 2920 Autochem II equipped with a thermal conductivity detector (TCD) for monitoring H$_2$ uptake/desorption. Catalyst samples were cooled to −50° C. in He (UHP, National Welders), then the gas switched to 5% H$_2$/Ar (certified, Machine and Welding Supply). Catalysts were heated at 10° C./min to 400° C. and held for 1 h. Hydride decomposition experiments were performed on Pd-containing samples by cooling to −50° C. in H$_2$/Ar after 400° C. reduction. A second ramp at 10° C./min to 400° C. then proceeded to give TPHD profiles.

Because the interstitial hydride forms in the palladium fcc lattice, if the palladium particles are smaller, or if the electronic structure is modified by substitution of another metal (alloying), the H/Pd ratio will decrease. The TPHD results are consistent with the higher dispersions of the tetraammine-derived palladium on alumina catalysts. Without being bound by theory, the suppression of TPHD peaks for the bimetallic catalysts as compared to the monometallic catalysts suggests PdRe alloy formation.

Figure 10:
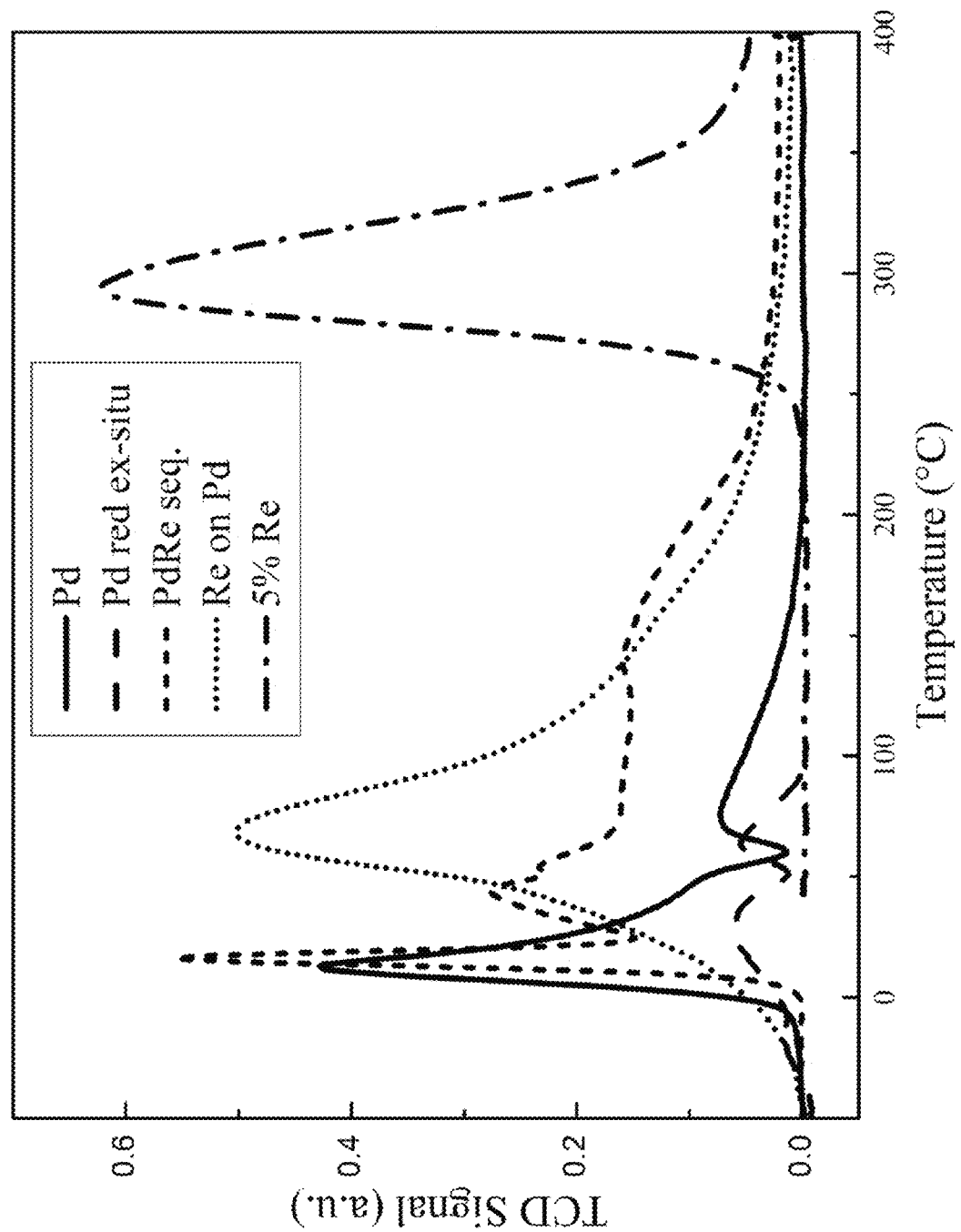
FIG. 10 shows TPR profiles obtained from further exemplary catalysts.

FIG. 10 shows TPR profiles for a series of catalysts made with Grace alumina. The Pd* catalyst shown in FIG. 10 is a reduced and passivated monometallic palladium on alumina catalyst made with Pd TA as the palladium precursor. The TPR profile of the palladium-first sequential catalyst (labeled "Re on Pd/Al$_2$O$_3$") is shown in FIG. 10 in the blue trace, and is compared to the rhenium-first sequential catalyst made with Pd TA and ammonium perrhenate, at a 1:1 Pd:Re ratio, shown in the red trace.

The TPR profile of the palladium-first sequentially-impregnated catalyst contains a peak at ~70° C. with a tail that extends to nearly 400° C. Most of this H$_2$ uptake is associated with rhenium reduction (7.5 H/Re), whereas reduction of the palladium in the parent monometallic catalyst contributes minimally and only at low temperatures (as shown by the dashed trace). CO chemisorption results for these catalysts are given in Tables 5a and 5b.

TABLE 4

Quantitative TPHD results.

| Al$_2$O$_3$ (G) support | | Al$_2$O$_3$ (S) support | |
|---|---|---|---|
| Catalyst | H/Pd | Catalyst | H/Pd |
| Pd-nitrate** | 0.564 | Pd-tetraammine** | 0.088 |
| Pd-tetraammine** | 0.243 | PdRe seq | 0.092 |
| PdRe seq | 0.077 | PdRe co | 0.114 |
| PdRe (1:2) seq | 0.116 | (not tested) | (not tested) |
| PdRe co | 0.051 | (not tested) | (not tested) |

**indicates metal precursor

TABLE 5a

CO chemisorption.

| | Dispersion (%) | |
|---|---|---|
| Catalyst | Metals basis | Pd basis |
| Grace Al$_2$O$_3$ support | | |
| Re on Pd/Al$_2$O$_3$ (1:1) | 17 | 39 |
| PdRe DCS | 14 | 55 |
| Strem Al$_2$O$_3$ support | | |
| Re on Pd/Al$_2$O$_3$ | 18 | 43 |
| PdRe DCS | 12 | 47 |

TABLE 5b

CO (analysis at 35° C.) and H$_2$ chemisorption results

| | CO chemisorption | | | | H$_2$ chemisorption | | | |
|---|---|---|---|---|---|---|---|---|
| | | | 35° C. | | 70° C. uptake | | 100° C. uptake | |
| Catalyst | CO uptake (μmol/g$_{cat}$) | CO/ metal | uptake (μmol H$_2$/g$_{cat}$) | H/ metal | (μmol H$_2$/g$_{cat}$) | H/ metal | (μmol H$_2$/g$_{cat}$) | H/ metal |
| Pd (NO$_3$) | 29.3 | 0.102 | 15.3 | 0.107 | 14.1 | 0.099 | 10.2 | 0.071 |
| Pd (TA) | 105 | 0.373 | 49.7 | 0.353 | 42.2 | 0.299 | 41.3 | 0.293 |
| PdRe co. | 45.5 | 0.082 | 12.3 | 0.045 | 12.3 | 0.045 | 11.6 | 0.042 |
| Re on Pd | 33.9 | 0.068 | 3.9 | 0.016 | 5.6 | 0.022 | 9.3 | 0.037 |
| PdRe seq. (350) | 87.7 | 0.172 | 14.3 | 0.056 | 16.0 | 0.063 | 21.6 | 0.084 |
| PdRe seq. (400) | 104 | 0.193 | 13.6 | 0.050 | 14.9 | 0.055 | 23.2 | 0.086 |
| PdRe (1:2) seq. | 96.5 | 0.124 | 6.3 | 0.016 | 15.2 | 0.039 | 26.9 | 0.069 |
| Re (H) | 28.9 | 0.098 | 1.4 | 0.010 | 4.1 | 0.028 | 5.9 | 0.040 |
| Re (N) | 37.1 | 0.138 | 3.2 | 0.024 | 10.0 | 0.074 | 10.2 | 0.076 |

The metal dispersion of these catalysts on a total metals basis and a Pd-only basis are similar to the catalysts described in Tables 2 and 3. The dispersions on a total metals basis for the DCS-derived catalysts are lower because of the 1:2 Pd:Re stoichiometry present in the DCS salt.

Figure 11:
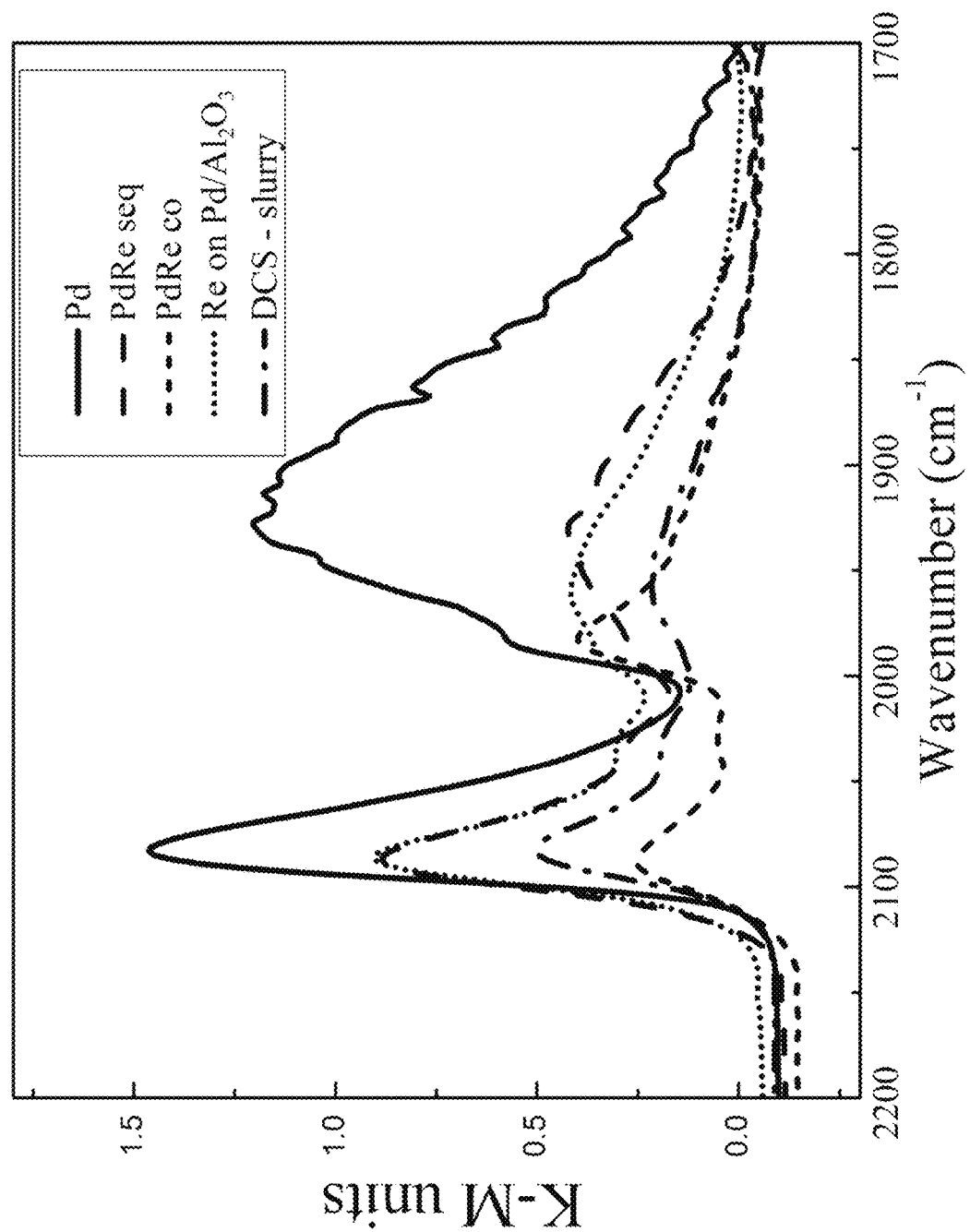
FIG. 11 shows CO DRIFTS spectra obtained from additional exemplary catalysts.

CO DRIFT spectra of a series of catalysts made using Grace alumina are shown in FIG. 11. In this figure, the Pd-only catalyst used Pd TA, the co-impregnated catalyst used Pd nitrate at a 1:1 Pd:Re ratio (3 wt % Pd and 5 wt % Re), and the sequential catalyst is a Re-first sequential catalyst using Pd TA as the palladium precursor and ammonium perrhenate also at a 1:1 Pd:Re ratio (3 wt % Pd and 5 wt % Re). The DCS catalyst was made as described in Example 4, using Pd nitrate.

The spectra contain peaks assigned to linear (atop) CO on palladium, atop CO on rhenium, and two-fold bridging CO on palladium. The spectrum of the palladium-first sequentially-impregnated catalyst (labeled "Re on Pd/$Al_2O_3$") is shown by the green trace, exhibits a high linear/bridging ratio, and is similar to that of the rhenium-first sequentially-impregnated catalyst (labeled "PdRe seq"), except the bridging CO band is shifted to higher wavenumbers. The spectrum of the DCS-derived catalyst is similar; however, the overall intensity (Kubelka-Munk units) is lower.

Figure 12:
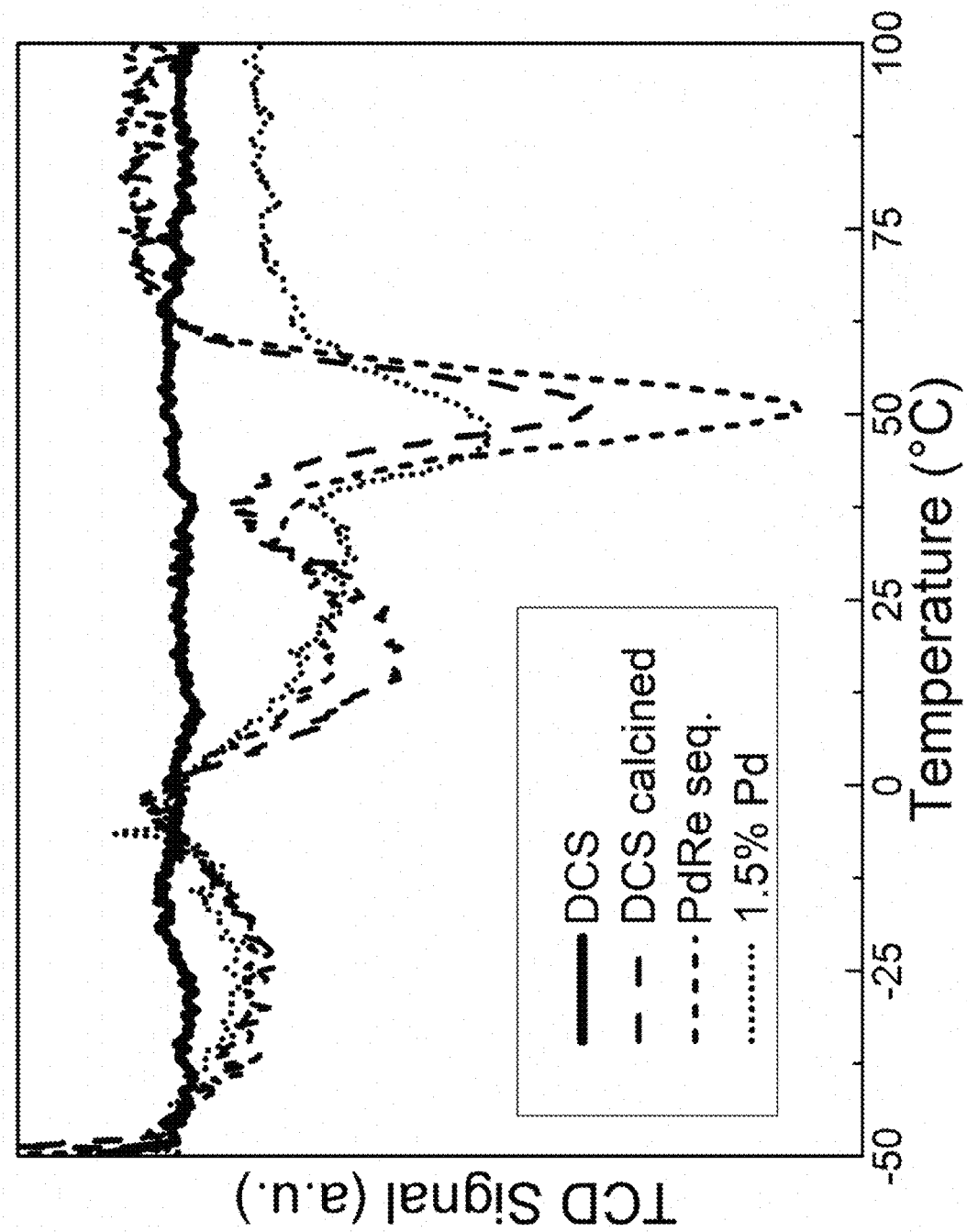
FIG. 12 shows the TPHD profiles obtained from additional exemplary catalysts.

TPHD profiles of a series of catalysts made using Grace alumina are shown in FIG. 12, under an atmosphere of 5% $H_2$/Ar. In this figure, the Pd-only catalyst used Pd TA and the sequential catalyst is a Re-first sequential catalyst using Pd TA as the palladium precursor and ammonium perrhenate at a 1:1 Pd:Re ratio (3 wt % Pd and 5 wt % Re). The DCS catalysts were made as described in Example 4.

A $H_2$ desorption peak associated with β-$PdH_x$ decomposition appears at ~40° C. for the palladium on alumina catalysts. Diminution and shifting of this peak provides evidence of changes in the palladium particle size and the Pd—Re interactions in the bimetallic catalysts. The β-$PdH_x$ decomposition peak is completely suppressed in the TPHD profiles of the DCS-derived catalysts, owing to the 1:2 Pd:Re ratio and strong interaction between the metals.

The TPR and TPHD data for the DCS catalyst indicate substantial metal-metal interaction, as shown by the single TPR peak at ~200° C., and nearly complete suppression of β-Pd hydride formation in the TPHD profile.

Figure 13:
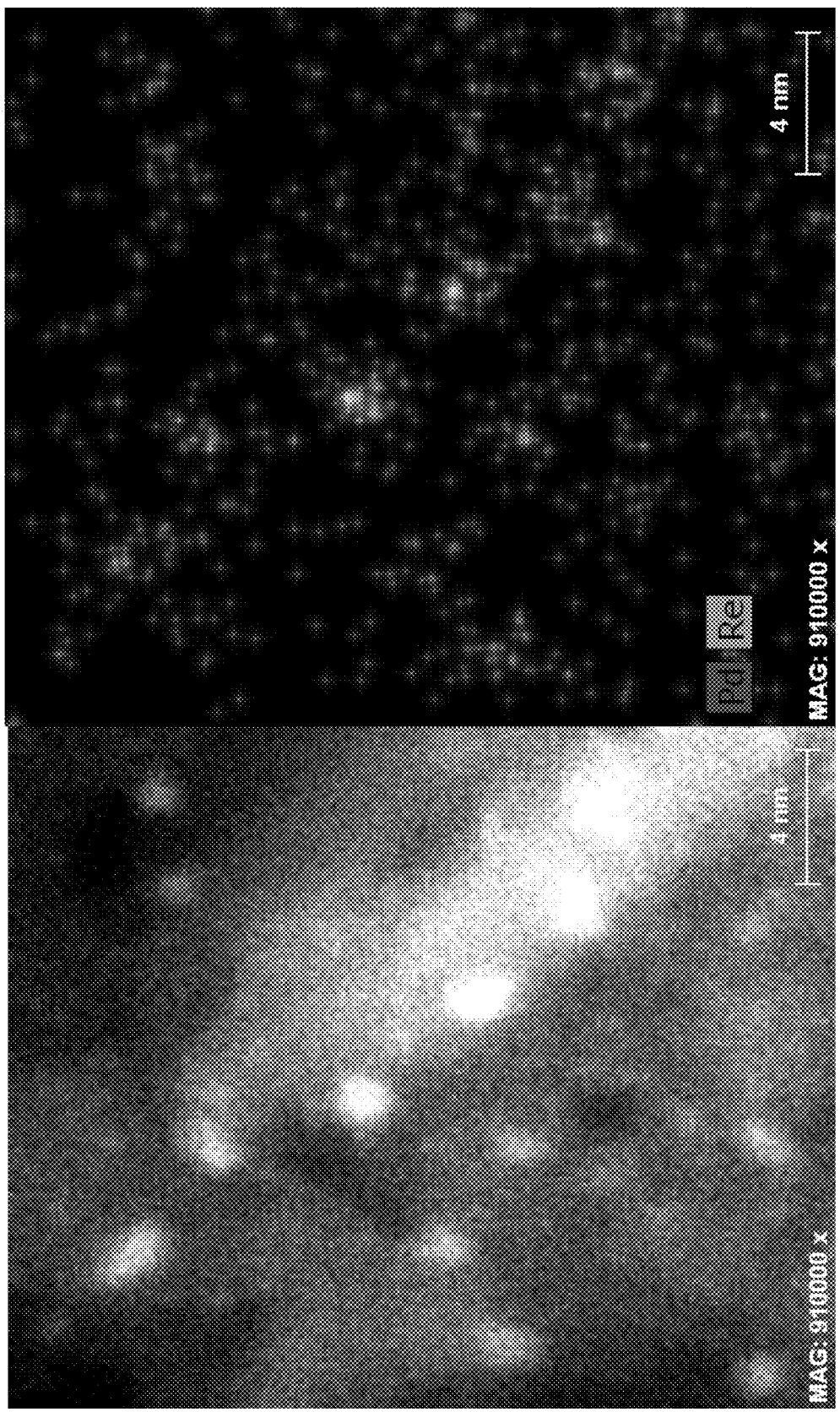
FIG. 13(a) is a high-angle annular dark field (HAADF) scanning TEM image of an exemplary catalyst.
FIG. 13(b) is an energy dispersive x-ray (EDX) analysis of the same catalyst.

FIG. 13(a) shows the high-angle annular dark field (HAADF)-scanning transmission electron microscopy (STEM) image of the DCS-derived catalyst, revealing supported metal particles 2-3 nm in diameter. Energy dispersive x-ray (EDX) analysis mapping of the same region as the image of FIG. 13(a) indicates that these metal particles contain both Pd (shown in red) and Re (shown in green), as seen by the substantial overlap of the red and green colors in FIG. 13(b). These images show that very small particles (≤2 nm) are present in this catalyst, and that both palladium and rhenium atoms are present in single particles, indicating alloying. The intimate contact of palladium and rhenium in the DCS-derived catalyst in comparatively small metal particles suggests enhanced activity and selectivity in hydrogenation reactions.

Example 7

Hydrogenation of Furfural

The hydrogenation of furfural was conducted at 150° C. and ambient pressure in a fixed-bed flow microreactor. Catalysts were reduced for 1 hour in situ at 400° C. in flowing $H_2$ prior to the addition of the aldehyde. Furfural was fed via syringe pump, mixed with $H_2$ in an approximate 1:7.4 molar ratio, and evaporated before contacting the catalyst. Differential conversions of furfural (<10%) were achieved by adjusting the weight-hourly space velocity (20-200 $h^{-1}$) in order to determine reaction rates. Furfural was typically added at the appropriate rate consistent with 50 mg of catalyst used, but the amount of catalyst used varied from between about 25 to about 250 mg. Turnover frequencies (TOF) were calculated using CO uptake values (moles/g catalyst) from volumetric chemisorption at 35° C. The rhenium-only catalysts were inactive under the test conditions. Under the test conditions, ring-opened products (i.e., butanol, pentanol) were absent.

Figure 14:
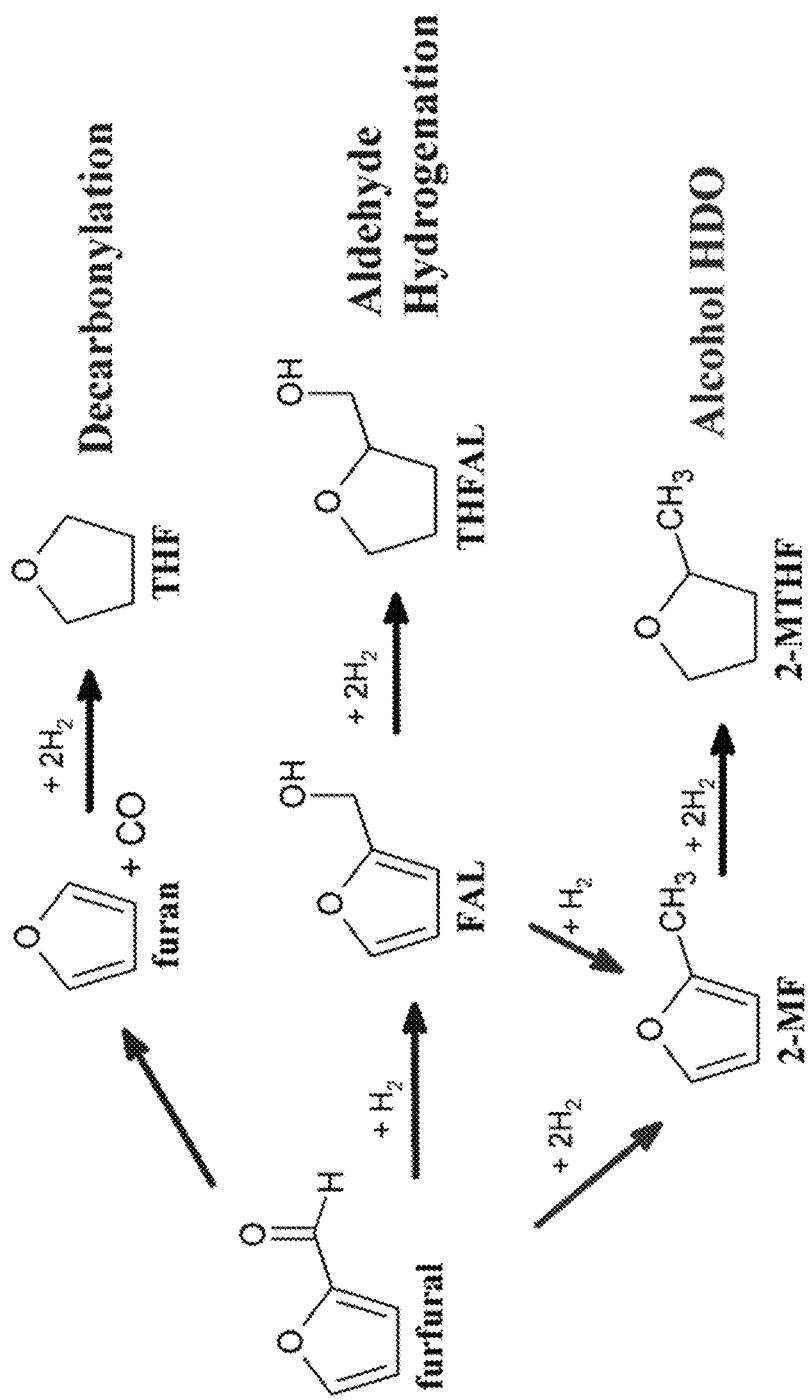
FIG. 14 is a reaction scheme showing potential reaction products from the hydrogenation of furfural.

FIG. 14 illustrates potential reaction pathways and products for the hydrogenation of furfural with the catalysts disclosed herein. Hydrogenation of the aldehyde moiety to produce furfuryl alcohol (FAL) was the desired pathway in this study (the middle pathway in FIG. 14). Decarbonylation of the furfural to furan could also occur (the upper pathway in FIG. 14). Hydrodeoxygenation (HDO) to 2-methyl furan (2-MF) is also possible (the lower pathway in FIG. 14). Ring saturation of these primary products to their tetrahydrofuran (THF) analogues may also occur as a result of excessive hydrogenation (i.e. over-reduction).

Figure 15:
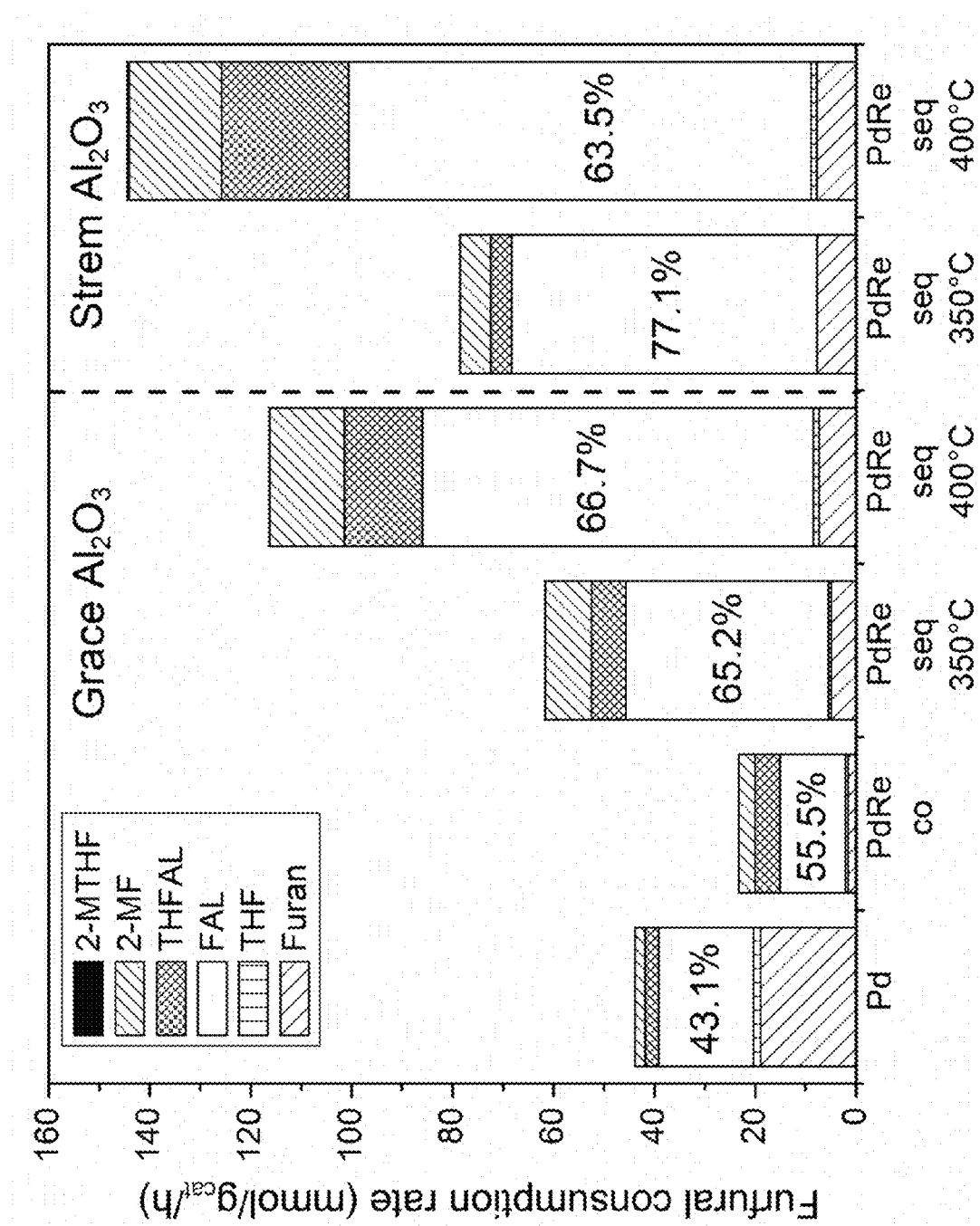
FIG. 15 is a graph of the aldehyde consumption rate of exemplary catalysts, showing also the selectivity of each catalyst.

Furfural consumption and product formation rates are shown in FIG. 15 for a series of catalysts. The temperatures refer to calcination at either 350° C. for 1 h or 400° C. for 3 h after each impregnation step, for the sequentially-impregnated catalysts. Abbreviations used: tetrahydrofuran (THF), furfuryl alcohol (FAL), tetrahydrofurfuryl alcohol (THFAL), 2-methyl furan (2-MF), and 2-methyl THF (2-MTHF). For this study, the Pd-only catalysts use the palladium precursor noted, the co-impregnated catalyst used Pd nitrate, and the sequential catalysts are all Re-first sequential catalysts using Pd TA as the palladium precursor. Ratios of Pd:Re are 1:1 unless otherwise noted. The production rates are also shown in Tables 6a and 6b.

TABLE 6a

Production Rates for Product Formation.

| | Production rates (mmol/$g_{cat}$/h) | | | | | |
|---|---|---|---|---|---|---|
| | FAL | THFAL | Furan | THF | 2-MF | 2-MTHF |
| | Grace $Al_2O_3$ | | | | | |
| Pd ($NO_3$) | 5.8 | 0.9 | 3.9 | 0.2 | 0.1 | 0.0 |
| Pd (TA) | 18.8 | 2.6 | 19.0 | 1.4 | 2.0 | 0.0 |
| PdRe co. | 12.9 | 5.0 | 1.6 | 0.6 | 3.2 | 0.0 |
| PdRe seq. (350) | 40.2 | 6.8 | 5.0 | 0.5 | 9.1 | 0.0 |
| PdRe seq. (400) | 77.6 | 15.4 | 7.4 | 1.1 | 14.9 | 0.0 |
| | Strem $Al_2O_3$ | | | | | |
| PdRe seq. (350) | 60.5 | 4.1 | 7.8 | 0.0 | 6.0 | 0.0 |
| PdRe seq. (400) | 91.7 | 25.1 | 7.9 | 1.1 | 18.3 | 0.4 |

TABLE 6b

TOFs (min$^{-1}$) at 150° C.
using volumetric H$_2$ and CO chemisorption uptake at 35° C.

| basis | furfural | | FAL | | furan | | 2-MF | | THFAL | |
|---|---|---|---|---|---|---|---|---|---|---|
| | CO | H | CO | H | CO | H | CO | H | CO | H |
| Pd (NO$_3$) | 6.2 | 5.7 | 3.3 | 3.1 | 2.2 | 2.1 | 0.0 | 0.0 | 0.5 | 0.5 |
| Pd (TA) | 6.9 | 7.3 | 3.0 | 3.2 | 3.0 | 3.2 | 0.3 | 0.3 | 0.4 | 0.4 |
| PdRe co. | 8.6 | 15.8 | 4.7 | 8.8 | 0.6 | 1.1 | 1.2 | 2.2 | 1.8 | 3.4 |
| Re on Pd | 21.4 | 92.0 | 14.2 | 61.2 | 0.7 | 3.2 | 1.9 | 8.3 | 4.3 | 18.3 |
| PdRe seq. (350) | 11.7 | 35.9 | 7.6 | 23.4 | 0.9 | 2.9 | 1.7 | 5.3 | 1.3 | 4.0 |
| PdRe seq. (400) | 18.6 | 71.2 | 12.4 | 47.5 | 1.2 | 4.5 | 2.4 | 9.1 | 2.5 | 9.4 |
| PdRe (1:2) seq. | 3.0 | 23.4 | 2.2 | 16.7 | 0.2 | 1.9 | 0.3 | 2.3 | 0.3 | 2.2 |

The sequentially-impregnated catalysts show greater activity and FAL selectivity than the co-impregnated and monometallic palladium catalysts. Moreover, greater activity is observed for the sequential catalysts that were calcined at 400° C. than the sequential catalysts that were calcined at 350° C. The higher FAL selectivity seen with the bimetallic catalysts appears to occur at the expense of furan formation, as furan results from decarbonylation of furfural. The sequential catalyst prepared using Strem alumina and calcined at 400° C. exhibits a furfural consumption rate that is about 8 times greater than that of the palladium-only catalysts and bimetallic co-impregnated catalysts, along with higher FAL selectivity (as shown in Table 7).

TABLE 7

Selective hydrogenation of furfural with catalysts supported on Strem alumina.

| Catalyst | Furfural consumption rate (mmol/gcat/h) | Furfural TOF (#/site/min)* | FAL production rate (mmol/gcat/h) | FAL Selectivity (%) | FAL TOF (#/site/min)* |
|---|---|---|---|---|---|
| Pd | 20.1 | 3.2 | 8.2 | 41.0 | 1.3 |
| PdRe co. | 18.0 | 5.1 | 11.0 | 60.9 | 3.1 |
| PdRe seq. (350° C.) | 78.5 | 13.6 | 60.5 | 77.1 | 10.5 |
| PdRe seq. (400° C.) | 144 | 24.3 | 91.7 | 63.5 | 15.4 |

*Based on CO chemisorption uptake for bimetallic catalysts.

The FAL formation rate for the sequential catalyst prepared using Strem alumina and calcined at 400° C. is about 13 times higher than that of the palladium-only catalysts, and about 8 times higher than the bimetallic co-impregnated catalysts. Turnover frequencies (TOFs) for furfural consumption and FAL formation, calculated based on CO volumetric chemisorption measurements, are also higher for the sequentially-impregnated catalysts.

The results suggest that the presence of rhenium inhibits the undesired palladium-catalyzed furfural decarbonylation to furan, and instead creates catalytic sites that are highly active for the selective hydrogenation of furfural to FAL. The sequential impregnation process appears to generate a greater density of these active sites than co-impregnation, and these active sites comprise adjacent Pd and Re species, suggesting direct interaction of zero-valent rhenium with palladium.

The effect of calcination temperature and time cannot be explained simply by a change in metal particle size, as the dispersions measured by CO chemisorption are similar for these catalysts (Table 8).

TABLE 8

Metal dispersions and TOFs for bimetallic catalysts.

| Catalyst* | Calcination T (° C.) | Dispersion (%) | | TOF (#/site/min) | | | |
|---|---|---|---|---|---|---|---|
| | | Metal | Pd | Furfural | FAL | furan | 2-MF |
| Pd (NO$_3$) | 350 | 15.6 | 15.6 | 9.9 | 5.3 | 3.5 | 0.1 |
| Pd (TA) | 350 | 56.0 | 56.0 | 6.9 | 3.0 | 3.0 | 0.3 |
| PdRe co | 350 | 10.4 | 24.1 | 8.6 | 4.7 | 0.6 | 1.2 |
| PdRe (1:1) seq | 350 | 19.6 | 46.7 | 11.7 | 7.6 | 0.9 | 1.7 |
| PdRe (1:1) seq | 400 | 23.2 | 55.5 | 18.6 | 12.4 | 1.2 | 2.4 |
| PdRe (1:1) seq** | 350 | 21.5 | 51.2 | 13.6 | 10.5 | 1.3 | 1.0 |
| PdRe (1:1) seq** | 400 | 22.1 | 52.8 | 24.3 | 15.4 | 1.3 | 3.1 |

*Nominal loadings: 3 wt % Pd and 5 wt % Re (for bimetallic catalysts).
**Strem support The FAL TOFs appear to be affected by the preparation method and the calcination conditions, suggesting that sequential impregnation with a higher calcination temperature creates additional active sites for selective hydrogenation to FAL. Furthermore, the increased FAL selectivity cannot be explained solely by inhibition of undesired pathways, e.g., decarbonylation to furan. The furan TOFs of the sequentially-impregnated catalysts as compared to the palladium-only catalysts are similar despite a large difference in dispersion. Addition of rhenium to a catalyst decreases the furan TOF for all the bimetallic catalysts; however, the furan TOFs for the sequentially impregnated samples are generally similar. For the PdRe catalysts prepared by sequential impregnation, the TOFs for FAL and 2-methyl furan (2-MF) formation exhibit a similar dependence on calcination conditions.

Metal dispersions and TOFs for two palladium-first sequentially-impregnated catalysts are shown in Table 9.

TABLE 9

Metal dispersions and TOFs for Re-modified palladium-alumina catalysts.

| Catalyst* | Pd precursor | Dispersion (%) | | TOF (#/site/min) | | | |
|---|---|---|---|---|---|---|---|
| | | Metal | Pd | Furfural | FAL | furan | 2-MF |
| PdRe/Al$_2$O$_3$ (Grace) | Pd(NO$_3$)$_2$ | 7.6 | 18.0 | 21.4 | 14.2 | 0.7 | 1.9 |
| PdRe/Al$_2$O$_3$ (Strem) | Pd(TA) | 18.0 | 42.9 | 20.5 | 15.6 | 2.1 | 1.7 |

*Nominal loadings: 3 wt % Pd and 5 wt % Re

The palladium-alumina catalysts impregnated with rhenium were prepared using different precursors: Pd(NO$_3$) and Pd tetraammine (TA), which provided catalysts with different metal dispersions. The similar FAL TOFs and their near equivalence to the FAL TOFs of the sequentially-prepared bimetallic catalysts shown in Table 8 suggests the creation of similar surface sites, e.g., $ReO_x$ species on Pd particles.

Figure 16:
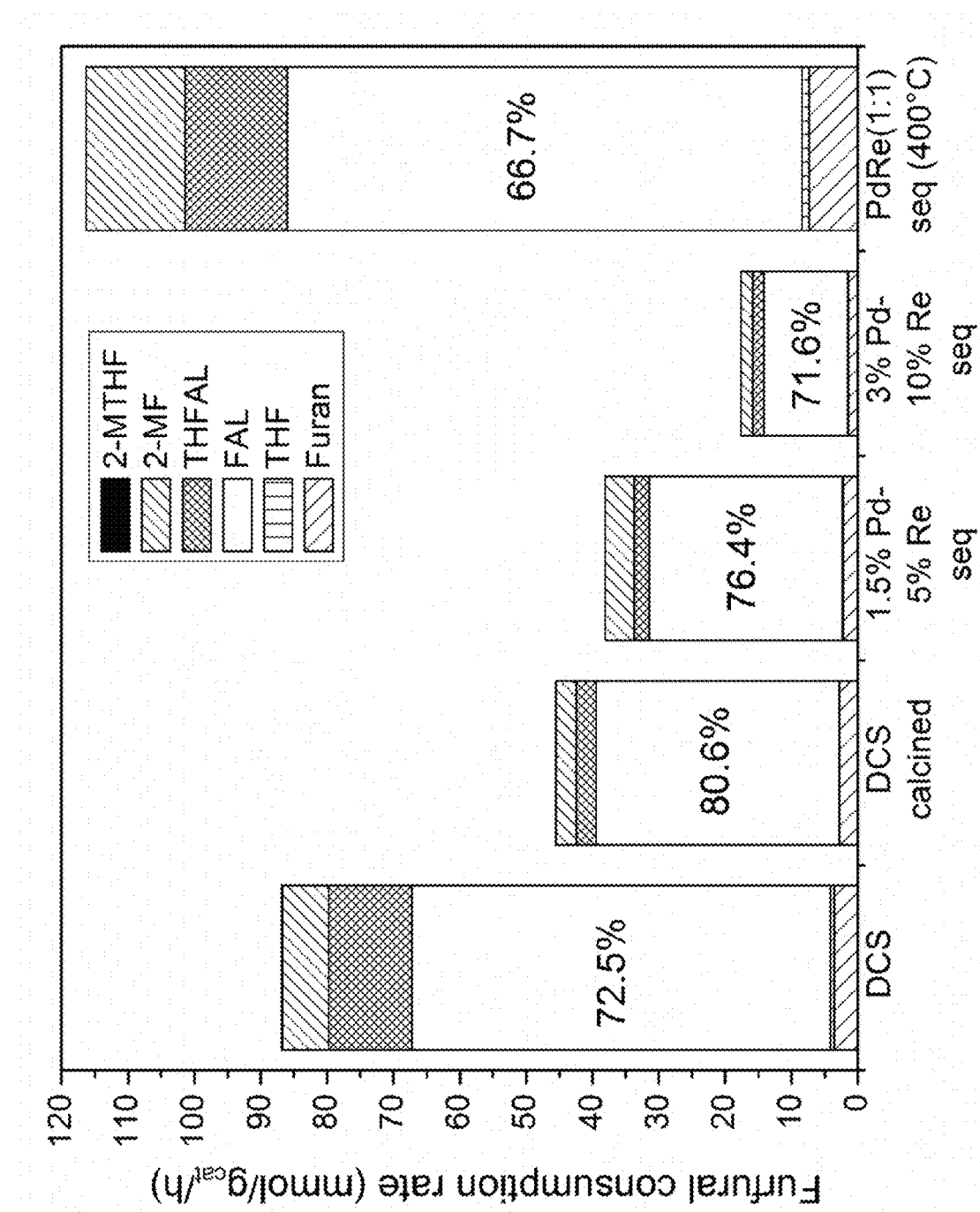
FIG. 16 is a graph of the aldehyde consumption rate of additional exemplary catalysts, showing also the selectivity of each catalyst.

Furfural consumption and product formation rates are shown in FIG. 16 for a series of catalysts including DCS catalysts. The DCS catalysts were prepared on Grace alumina as described in Example 4. The sequential catalysts were Re-first using Pd TA and ammonium perrhenate metal precursors. The production rates are also shown in Tables 10a and 10b.

TABLE 10a

Production Rates for Product Formation.

| | Production rates (mmol/$g_{cat}$/h) | | | | | |
|---|---|---|---|---|---|---|
| | FAL | THFAL | Furan | THF | 2-MF | 2-MTHF |
| DCS | 63.1 | 12.6 | 3.6 | 0.6 | 6.9 | 0.2 |
| DCS calcined | 36.7 | 3.0 | 2.8 | 0.0 | 3.0 | 0.0 |
| 1.5% Pd—5% Re seq. | 29.1 | 2.3 | 2.2 | 0.1 | 4.4 | 0.0 |
| 3% Pd—10% Re seq. | 12.6 | 1.7 | 1.4 | 0.1 | 1.8 | 0.0 |

TABLE 10b

ICP-OES analysis of PdRe/$Al_2O_3$ catalysts (loading of DCS and calcined DCS equivalent).

| Catalyst | Pd loading (wt %) | Re loading (wt %) |
|---|---|---|
| DCS | 1.41 | 4.72 |
| PdRe seq. | 1.50 | 4.85 |
| 1.5% Pd | 1.49 | — |
| 3% Pd | 3.00 | — |
| 5% Re | — | 5.02 |

As shown, the non-calcined DCS catalyst outperformed the other catalysts in furfural hydrogenation on a turnover frequency basis (20.4 h$^{-1}$ for furfuryl alcohol) and exhibited about 73% selectivity.

As seen in FIG. 16, a 1.5 wt % Pd-5 wt % Re bimetallic catalyst derived from the DCS without calcination and reduced in situ was less active than a 3.0 wt % Pd-5 wt % Re sequentially-impregnated bimetallic (400° C.) catalyst; however, the TOFs for furfural (consumption) and FAL (production) are the highest among the catalysts tested (Tables 11a, 11b and 11c).

TABLE 11a

Metal dispersions and TOFs for Pd:Re(1:2) DCS and sequential Grace alumina catalysts.

| | Metal (wt %)* | | Calcination T (° C.) | Dispersion (%) | | TOF (#/site/min) | | | |
|---|---|---|---|---|---|---|---|---|---|
| Catalyst | Pd | Re | | Metal | Pd | Furfural | FAL | furan | 2-MF |
| PdRe DCS | 1.5 | 5 | — | 14.3 | 54.8 | 28.1 | 20.4 | 1.2 | 2.2 |
| PdRe DCS | 1.5 | 5 | 350 | 18.8 | 71.9 | 11.2 | 9.1 | 0.7 | 0.8 |
| PdRe (1:2) seq | 1.5 | 5 | 400 | 20.4 | 78.1 | 8.6 | 6.6 | 0.5 | 1.0 |
| PdRe (1:2) seq | 3.0 | 10 | 350 | 13.8 | 51.3 | 3.0 | 2.2 | 0.3 | 0.3 |

*Nominal metal loadings.

TABLE 11b

CO and $H_2$ chemisorption specific uptake (μmol/$g_{cat}$ CO or $H_2$) and molar CO (or H)/metal ratio as determined by ICP-OES.

| | CO chemisorption | | $H_2$ chemisorption | | | | | |
|---|---|---|---|---|---|---|---|---|
| | | | 35° C. | | 70° C. $H_2$ | | 100° C. $H_2$ | |
| Catalyst | CO uptake | CO/ metal | $H_2$ uptake | H/ metal | up-take | H/ metal | up-take | H/ metal |
| DCS | 51.5 | 0.133 | 7.27 | 0.038 | 11.0 | 0.057 | 12.7 | 0.066 |
| DCS calcined | 67.6 | 0.175 | 5.96 | 0.031 | 19.3 | 0.100 | 17.2 | 0.089 |
| PdRe seq. | 73.4 | 0.183 | 7.64 | 0.038 | 11.8 | 0.059 | 16.1 | 0.080 |
| 1.5% Pd | 59.4 | 0.640 | 31.7 | 0.452 | 27.7 | 0.396 | 27.8 | 0.398 |
| 3% Pd | 105 | 0.373 | 49.7 | 0.353 | 42.2 | 0.299 | 41.3 | 0.293 |
| 5% Re | 37.1 | 0.138 | 3.2 | 0.024 | 10.0 | 0.074 | 10.2 | 0.076 |

TABLE 11c

TOFs (min$^{-1}$) based on CO and $H_2$ chemisorption uptake at 35° C.

| | Furfural | | FAL | | Furan | | 2-MF | | THFAL | |
|---|---|---|---|---|---|---|---|---|---|---|
| Basis | CO | H | CO | H | CO | H | CO | H | CO | H |
| DCS | 28.1 | 99.6 | 20.4 | 72.3 | 1.2 | 4.1 | 2.2 | 8.0 | 4.1 | 14.4 |
| DCS calcined | 11.2 | 63.6 | 9.1 | 51.3 | 0.7 | 3.9 | 0.8 | 4.3 | 0.7 | 4.1 |
| PdRe seq. | 8.6 | 41.5 | 6.6 | 31.8 | 0.5 | 2.4 | 1.0 | 4.8 | 0.5 | 2.5 |
| 3% Pd | 6.9 | 7.3 | 3.0 | 3.2 | 3.0 | 3.2 | 0.3 | 0.3 | 0.4 | 0.4 |

When the DCS-derived catalyst was calcined at 350° C. prior to in situ reduction, there was a large decrease in the furfural TOF and an increase in FAL selectivity. For comparison, a 1.5 wt % Pd-5 wt % Re sequentially-impregnated catalyst calcined at 400° C. exhibited similar (albeit lower) activity and selectivity to the calcined DCS-derived catalyst. A higher-loading 1:2 Pd:Re catalyst prepared by sequential impregnation (3 wt % Pd-10 wt % Re, Re-first using Pd TA and ammonium perrhenate metal precursors), had lower specific activity and TOFs. Thus, a 1:2 Pd:Re catalyst derived from the DCS without calcination leads to a catalyst morphology that is favorable for the selective hydrogenation of furfural to FAL. Moreover, testing of other catalysts with 1:2 Pd:Re ratios did not show an increase in furfural consumption activity, although FAL selectivities typically were higher compared to the 1:1 Pd:Re catalysts.

Figure 17:
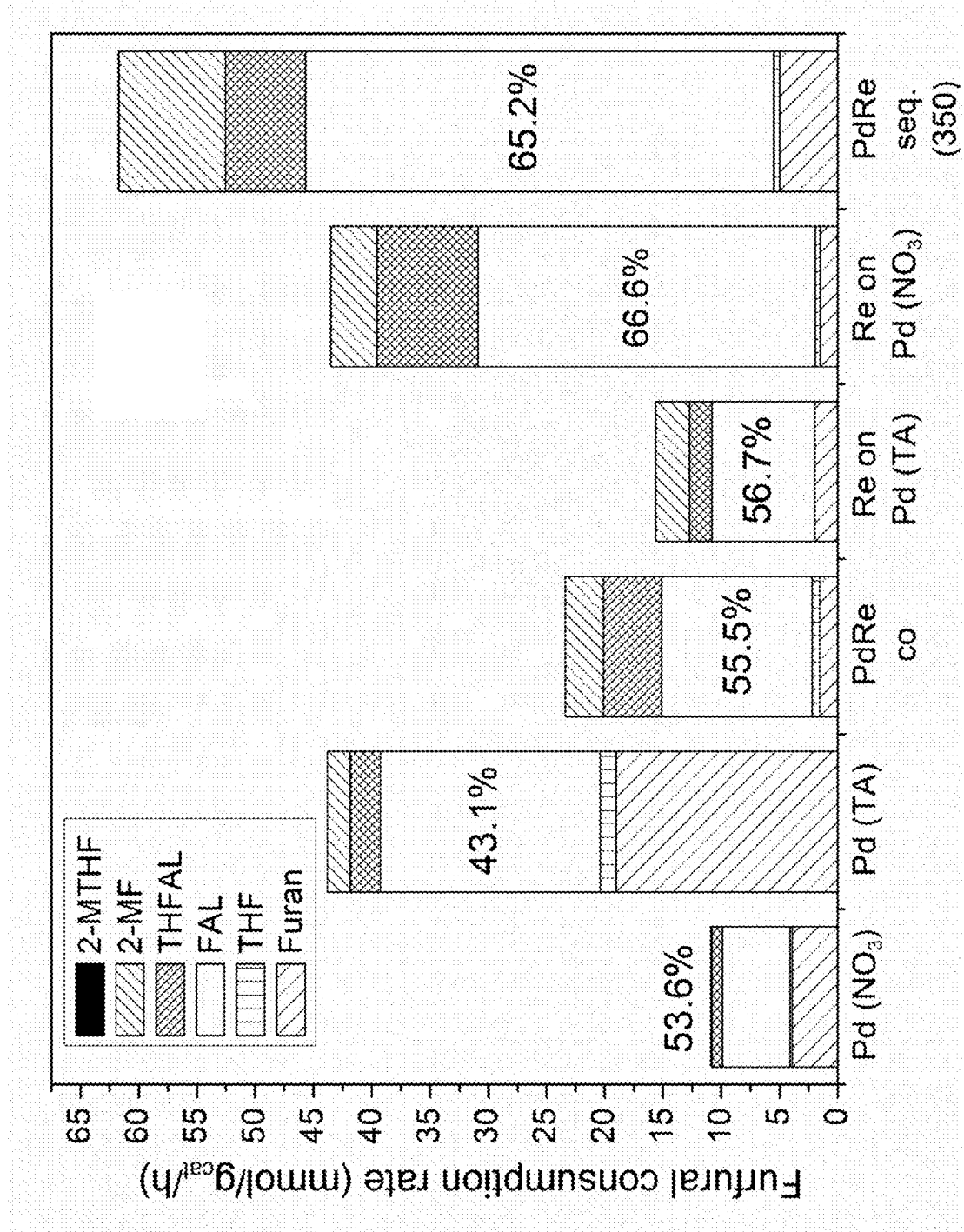
FIG. 17 is a graph of the aldehyde consumption rate of further exemplary catalysts, showing also the selectivity of each catalyst.

An analysis of the sequentially impregnated catalysts was also performed, comparing the catalysts made with the rhenium impregnated first (i.e. "Re-first" catalysts) with the catalysts made with the palladium impregnated first (i.e. "Pd-first" catalysts). FIG. 17 and Table 12 show the furfural consumption and product formation rates for a series of sequential catalysts prepared with Grace alumina.

The data labeled "Re on Pd" correspond to the product analyses and rate data for two Pd-first sequentially-impregnated catalysts, one made with the palladium TA precursor and one with the palladium nitrate precursor. The data labeled "PdRe seq. (350)" is the data from a Re-first catalyst calcined at 350° C.

As shown in FIG. 17, the catalyst prepared by depositing rhenium first, then palladium using palladium TA as the palladium precursor, onto Grace alumina and calcining at 350° C., exhibits an approximately fourfold higher furfural consumption rate and higher FAL selectivity than the Pd-first catalyst prepared with Pd TA as the palladium precursor, on Grace alumina, which was also calcined at 350° C. Also, the furfural consumption rate is approximately threefold higher than that measured for the corresponding Pd-first catalyst prepared with Pd nitrate as the palladium precursor, on Grace alumina, which was also calcined at 350° C.

TABLE 12

Metal dispersions and TOFs for a series of Grace catalysts.

| Basis | Furfural TOF (number/site/min) | | Furfuryl Alcohol TOF (number/site/min) | |
|---|---|---|---|---|
| | CO | H | CO | H |
| Pd (TA) | 6.9 | 7.3 | 3.0 | 3.2 |
| Pd (NO$_3$) | 6.2 | 5.7 | 3.3 | 3.1 |
| PdRe co | 8.6 | 15.8 | 4.7 | 8.8 |
| Re on Pd (TA) | 3.5 | 7.8 | 2.0 | 4.4 |
| Re on Pd (NO$_3$) | 21.4 | 92.0 | 14.2 | 61.2 |

Figure 18:
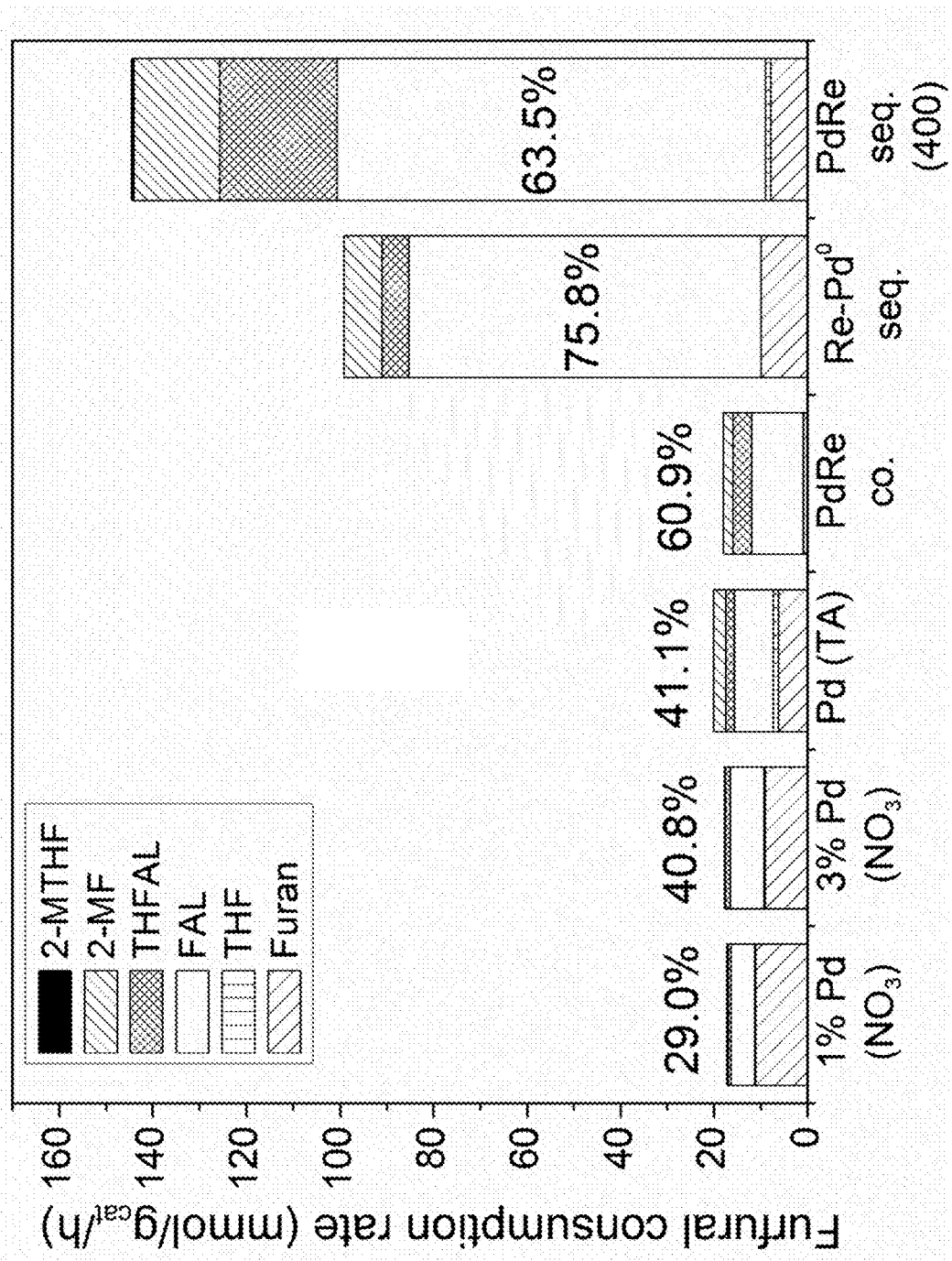
FIG. 18 is a graph of the aldehyde consumption rate of yet additional exemplary catalysts, showing also the selectivity of each catalyst.

FIG. 18 and Table 13 show the furfural consumption and product formation rates for a series of sequential catalysts prepared with Strem alumina. The data labeled "Re on Pd" is the data for a Pd-first sequentially-impregnated catalyst made with Pd TA as the palladium precursor, and the data labeled "PdRe seq. (400)" is the data from a Re-first catalyst calcined at 400° C. using Pd TA. Although similar trends are shown for the Re-first catalysts on Strem alumina as for Grace alumina, the magnitude is not as large.

TABLE 13

Metal dispersions and TOFs for a series of Strem catalysts.

| Basis | Furfural TOF (number/site/min) | | Furfuryl Alcohol TOF (number/site/min) | |
|---|---|---|---|---|
| | CO | H$_2$ | CO | H$_2$ |
| 1% Pd (NO$_3$) | 10.1 | 11.3 | 2.9 | 3.3 |
| 3% Pd (NO$_3$) | 10.1 | 9.4 | 4.1 | 3.8 |
| Pd (TA) | 3.2 | 3.7 | 1.3 | 1.5 |
| PdRe co | 5.1 | 5.6 | 3.1 | 3.4 |
| Re on Pd (TA) | 20.5 | 46.2 | 15.6 | 35.0 |

Example 8

Hydrogenation of 5-hydroxymethyl furfural (5-HMF)

Selective hydrogenation of 5-hydroymethyl furfural (5-HMF) was investigated using 3 wt. % Pd/Al$_2$O$_3$ and 3 wt. % Pd-5 wt. % Re/Al$_2$O$_3$ ("PdRe (1:1) seq. 400") catalysts in a batch reactor at 150° C. and 10 bar H$_2$ (initial pressure at 25° C.). The PdRe catalyst was made with Grace alumina with calcination performed at 400° C., is a Re-first sequential catalyst, and used Pd TA as the palladium precursor, prepared as described in Example 2.

Hydrogenation of 5-HMF was performed in a 100 mL Parr batch reactor. The catalyst (~100 mg) was reduced at 400° C. for 1 h in 40 mL/min H$_2$ in a fixed bed reactor. The reduced catalyst was transferred under N$_2$ to an inert atmosphere glove box, where ~25 mg was loaded into the reactor vessel along with 1 mmol 5-HMF, 25 mL THF (solvent) and a glass stir bar. The reactor was sealed, purged several times with H$_2$, and then charged to 10 bar H$_2$ at 25° C. The reactor was heated to 150° C. at 5° C./min and held for 1 h while stirring. Following the reaction, the vessel was cooled to room temperature, the contents filtered, and the liquid portion collected for testing by GC-FID. Samples were analyzed using a Shimadzu GC-2010 using a 30-m 5% polar capillary column (Restek RTX-5). The GC oven temperature program was as follows: 5-min hold at 30° C., ramp 10° C./min to 150° C., 10-min hold, 30° C./min ramp to 210° C., end program.

The reaction pathway to convert 5-HMF via hydrogenation to 2,5 bis(hydroxymethyl) furan (2,5-DHMF) is shown below:

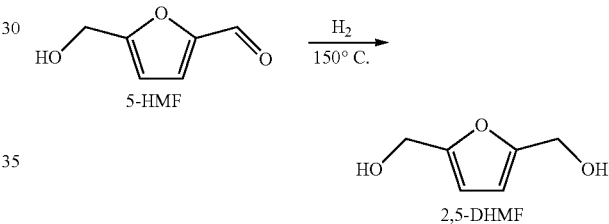

2,5-DHMF is a biorenewable aromatic monomer. Decarbonylation of 5-HMF to 2-hydroxymethyl furan (furfuryl alcohol) is an undesirable side reaction. Attempts to investigate this reaction in the gas-phase at 1 atm using a continuous fixed-bed reactor were unsuccessful due to the low vapor pressure and high thermal reactivity of 5-HMF. Tetrahydrofuran (THF) was chosen as the solvent because it is fully saturated and neither Pd/Al$_2$O$_3$ nor PdRe/Al$_2$O$_3$ showed any significant THF ring-opening activity in the gas-phase at 150° C.

GC-FID chromatograms of the reaction products obtained over Pd/Al$_2$O$_3$ and PdRe/Al$_2$O$_3$ after 1 hour of reaction time showed the data provided in Table 14. The values in the table are approximate yields since they are based on GC-FID area percentages.

TABLE 14

5-HMF and product peak areas from sample of reactor contents after 1 h reaction at 150° C.

| | Percent GC Area | |
|---|---|---|
| | Pd/Al$_2$O$_3$ | PdRe/Al$_2$O$_3$ seq. (400) |
| 5-HMF | 7.3 | 33.3 |
| 2,5-DHMF | 2.8 | 4.1 |
| FAL | 0 | 0 |
| 5-methyl furfural | 0.6 | 1.4 |

TABLE 14-continued

5-HMF and product peak areas from sample of
reactor contents after 1 h reaction at 150° C.

| | Percent GC Area | |
|---|---|---|
| | $Pd/Al_2O_3$ | $PdRe/Al_2O_3$ seq. (400) |
| 2,5-dimethyl furan | 2.8 | 15.1 |
| Unidentified* | 79.5 | 43.6 |

*Based on the retention time of these products and the reaction conditions, it is likely that they are primarily ring-saturated analogues of other compounds in the table.

From this data, it can be seen that higher 5-HMF conversion was obtained using $Pd/Al_2O_3$ (derived from Pd tetraammine (TA) nitrate) than with $PdRe/Al_2O_3$ under these conditions; however, the main products were unknown compounds that were tentatively ascribed to ring-saturation products. The GC retention times for 5-HMF, 2,5-DHMF, 2,5-dimethyl furan (2,5-DMF), 5-methyl furfural (5-MFal), furfural, furfuryl alcohol, THF and 2-methyl furan are known for comparison. In addition, $Pd/Al_2O_3$ produced low yields of 2,5-DMF, 2,5-DHMF, and 5-MFal. The $PdRe/Al_2O_3$ catalyst was less active than $Pd/Al_2O_3$; however, the sequentially prepared bimetallic catalyst was more selective for producing the desired 2-5-DHMF product.

This result shows that the sequential PdRe catalyst exhibits higher selectivity toward forming the desired 2,5-DHMF product than the Pd-only catalyst. The observed high selectivity to 2,5-DMF likely results from the hydrodeoxygenation (HDO) of 2,5-DHMF in a secondary reaction over the Pd:Re (1:1) seq. catalyst. Optimization of catalyst composition (Pd:Re ratio) and reaction conditions (temperature, pressure, time) may be effective in limiting secondary HDO reactions.

Various features and advantages of the invention are set forth in the following claims.

The invention claimed is:

1. A catalyst for the hydrogenation of an aldehyde, comprising
   a) an alumina support;
   b) rhenium adsorbed to the alumina support; and
   c) palladium adsorbed to the alumina support;
wherein the rhenium is adsorbed to the alumina support before the palladium is adsorbed to the alumina support.

2. The catalyst of claim 1, wherein the amount of rhenium in the catalyst is between about 4% and about 7% by weight, and wherein the amount of palladium in the catalyst is between about 0.5% and about 5% by weight.

3. The catalyst of claim 1, wherein the aldehyde is a furan-2-carbaldehyde.

4. The catalyst of claim 3, wherein the furan-2-carbaldehyde is furfural or 5-(hydroxymethyl)furfural.

5. The catalyst of claim 1, wherein the palladium is adsorbed to the alumina support by contacting the alumina with a solution of $Pd(NH_3)_4(NO_3)_2$.

6. The catalyst of claim 1, wherein the palladium is adsorbed to the alumina support by contacting the alumina with a solution of $Pd(NO_3)_2$.

7. The catalyst of claim 1, wherein the alumina support comprises gamma-alumina.

8. A method of making a catalyst for the hydrogenation of an aldehyde, comprising
   a) contacting an alumina support with a solution comprising rhenium to provide a first composition comprising an alumina support with rhenium absorbed thereto, and
   b) contacting the first composition with a solution comprising palladium to provide a second composition.

9. The method of claim 8, wherein the first composition is calcined prior to contacting the first composition with a solution comprising palladium.

10. The method of claim 8, wherein the solution of palladium has a pH of between about 9 and about 11.

11. The method of claim 8, wherein the amount of rhenium in the catalyst is between about 4% and about 7% by weight, and wherein the amount of palladium in the catalyst is between about 0.5% and about 5% by weight.

12. The method of claim 8, wherein the catalyst selectively hydrogenates the aldehyde to an alcohol.

13. The method of claim 8, wherein the aldehyde is a furan-2-carbaldehyde.

14. The method of claim 13, wherein the furan-2-carbaldehyde is furfural or 5-(hydroxymethyl)furfural.

15. The method of claim 8, wherein the alumina support comprises gamma-alumina.

16. The method of claim 8, wherein the solution comprising palladium comprises $Pd(NH_3)_4(NO_3)_2$.

17. The method of claim 8, wherein the solution comprising palladium comprises $Pd(NO_3)_2$.

18. A method of hydrogenating a furan-2-carbaldehyde to a 2-furanmethanol, comprising contacting a catalyst comprising rhenium, palladium and an alumina support with the furan-2-carbaldehyde in the presence of hydrogen to provide the 2-furanmethanol,
   wherein the catalyst was made by:
   (a) sequentially contacting a solution comprising rhenium and a solution comprising palladium with the alumina support; or
   (b) forming a salt comprising rhenium and palladium, and contacting a solution comprising the salt with the alumina support.

19. The method of claim 18, wherein the amount of rhenium in the catalyst is between about 4% and about 7% by weight, and wherein the amount of palladium in the catalyst is between about 0.5% and about 5% by weight.

20. The method of claim 18, wherein the catalyst was made by sequentially contacting a solution comprising rhenium and a solution comprising palladium with the alumina support, and wherein the alumina support was contacted with the solution comprising rhenium before the solution comprising palladium.

21. The method of claim 18, wherein the catalyst was made by sequentially contacting a solution comprising rhenium and a solution comprising palladium with the alumina support, and wherein the solution comprising palladium comprises $Pd(NH_3)_4(NO_3)_2$.

22. The method of claim 18, wherein the catalyst was made by sequentially contacting a solution comprising rhenium and a solution comprising palladium with the alumina support, and wherein the solution comprising palladium comprises $Pd(NO_3)_2$.

23. The method of claim 18, wherein the catalyst was made by forming a salt of rhenium and palladium, and contacting a solution comprising the salt with the alumina support, and wherein the ratio of palladium:rhenium is about 1:2.

24. The method of claim 23, wherein the salt is $[Pd(NH_3)_4(ReO_4)_2]$.

25. The method of claim 18, wherein the alumina support comprises gamma-alumina.

26. The method of claim 18, wherein the furan-2-carbaldehyde is furfural or 5-(hydroxymethyl)furfural.

* * * * *